(12) United States Patent
el Kaliouby et al.

(10) Patent No.: US 11,484,685 B2
(45) Date of Patent: Nov. 1, 2022

(54) ROBOTIC CONTROL USING PROFILES

(71) Applicant: Affectiva, Inc., Boston, MA (US)

(72) Inventors: Rana el Kaliouby, Milton, MA (US); Jason Krupat, Needham, MA (US)

(73) Assignee: Affectiva, Inc., Boston, MA (US)

( * ) Notice: Subject to any disclaimer, the term of this patent is extended or adjusted under 35 U.S.C. 154(b) by 55 days.

(21) Appl. No.: 16/914,546

(22) Filed: Jun. 29, 2020

(65) Prior Publication Data

US 2020/0324072 A1 Oct. 15, 2020

Related U.S. Application Data

(63) Continuation-in-part of application No. 16/781,334, filed on Feb. 4, 2020, which is a continuation-in-part
(Continued)

(51) Int. Cl.
*G06K 9/00* (2022.01)
*A61M 21/00* (2006.01)
(Continued)

(52) U.S. Cl.
CPC .......... *A61M 21/00* (2013.01); *A61B 5/0077* (2013.01); *A61B 5/165* (2013.01); *B25J 11/0005* (2013.01);
(Continued)

(58) Field of Classification Search
CPC .......... A61M 21/00; A61M 2021/0022; A61M 2021/0027; A61M 2021/0044;
(Continued)

(56) References Cited

U.S. PATENT DOCUMENTS 3,034,500 A 5/1962 Backster, Jr.
3,548,806 A 12/1970 Fisher
(Continued)

FOREIGN PATENT DOCUMENTS

JP 08115367 7/1996
KR 10-2005-0021759 A 3/2005
(Continued)

OTHER PUBLICATIONS

Rana Ayman El Kaliouby, Mind-reading machines: automated inference of complex mental states, Jul. 2005, University of Cambridge, Cambridge, United Kingdom.
(Continued)

*Primary Examiner* — Jonathan S Lee
(74) *Attorney, Agent, or Firm* — Adams Intellex, PLC

(57) ABSTRACT

Techniques for robotic control using profiles are disclosed. Cognitive state data for an individual is obtained. A cognitive state profile for the individual is learned using the cognitive state data that was obtained. Further cognitive state data for the individual is collected. The further cognitive state data is compared with the cognitive state profile. Stimuli are provided by a robot to the individual based on the comparing. The robot can be a smart toy. The cognitive state data can include facial image data for the individual. The further cognitive state data can include audio data for the individual. The audio data can be voice data. The voice data augments the cognitive state data. Cognitive state data for the individual is obtained using another robot. The cognitive state profile is updated based on input from either of the robots.

25 Claims, 15 Drawing Sheets

Related U.S. Application Data of application No. 16/726,647, filed on Dec. 24, 2019, which is a continuation-in-part of application No. 16/146,194, filed on Sep. 28, 2018, now abandoned, application No. 16/914,546, which is a continuation-in-part of application No. 15/861,866, filed on Jan. 4, 2018, now abandoned, said application No. 16/781,334 is a continuation-in-part of application No. 15/273,765, filed on Sep. 23, 2016, now abandoned, said application No. 15/861,866 is a continuation-in-part of application No. 15/273,765, filed on Sep. 23, 2016, now abandoned, said application No. 16/146,194 is a continuation-in-part of application No. 15/061,385, filed on Mar. 4, 2016, now abandoned, which is a continuation-in-part of application No. 14/848,222, filed on Sep. 8, 2015, now Pat. No. 10,614,289, said application No. 15/273,765 is a continuation-in-part of application No. 14/796,419, filed on Jul. 10, 2015, now abandoned, which is a continuation-in-part of application No. 14/460,915, filed on Aug. 15, 2014, now abandoned, said application No. 14/848,222 is a continuation-in-part of application No. 14/460,915, filed on Aug. 15, 2014, now abandoned, said application No. 15/061,385 is a continuation-in-part of application No. 13/249,317, filed on Sep. 30, 2011, now abandoned, said application No. 14/460,915 is a continuation-in-part of application No. 13/153,745, filed on Jun. 6, 2011, now abandoned.

(60) Provisional application No. 62/955,493, filed on Dec. 31, 2019, provisional application No. 62/954,819, filed on Dec. 30, 2019, provisional application No. 62/954,833, filed on Dec. 30, 2019, provisional application No. 62/926,009, filed on Oct. 25, 2019, provisional application No. 62/925,990, filed on Oct. 25, 2019, provisional application No. 62/893,298, filed on Aug. 29, 2019, provisional application No. 62/827,088, filed on Mar. 31, 2019, provisional application No. 62/679,825, filed on Jun. 3, 2018, provisional application No. 62/637,567, filed on Mar. 2, 2018, provisional application No. 62/625,274, filed on Feb. 1, 2018, provisional application No. 62/611,780, filed on Dec. 29, 2017, provisional application No. 62/593,440, filed on Dec. 1, 2017, provisional application No. 62/593,449, filed on Dec. 1, 2017, provisional application No. 62/557,460, filed on Sep. 12, 2017, provisional application No. 62/541,847, filed on Aug. 7, 2017, provisional application No. 62/524,606, filed on Jun. 25, 2017, provisional application No. 62/503,485, filed on May 9, 2017, provisional application No. 62/469,591, filed on Mar. 10, 2017, provisional application No. 62/448,448, filed on Jan. 20, 2017, provisional application No. 62/442,325, filed on Jan. 4, 2017, provisional application No. 62/442,291, filed on Jan. 4, 2017, provisional application No. 62/370,421, filed on Aug. 3, 2016, provisional application No. 62/301,558, filed on Feb. 29, 2016, provisional application No. 62/273,896, filed on Dec. 31, 2015, provisional application No. 62/265,937, filed on Dec. 10, 2015, provisional application No. 62/222,518, filed on Sep. 23, 2015, provisional application No. 62/217,872, filed on Sep. 12, 2015, provisional application No. 62/128,974, filed on Mar. 5, 2015, provisional application No. 62/082,579, filed on Nov. 20, 2014, provisional application No. 62/047,508, filed on Sep. 8, 2014, provisional application No. 62/023,800, filed on Jul. 11, 2014, provisional application No. 61/972,314, filed on Mar. 30, 2014, provisional application No. 61/953,878, filed on Mar. 16, 2014, provisional application No. 61/927,481, filed on Jan. 15, 2014, provisional application No. 61/924,252, filed on Jan. 7, 2014, provisional application No. 61/916,190, filed on Dec. 14, 2013, provisional application No. 61/867,007, filed on Aug. 16, 2013, provisional application No. 61/467,209, filed on Mar. 24, 2011, provisional application No. 61/447,464, filed on Feb. 28, 2011, provisional application No. 61/447,089, filed on Feb. 27, 2011, provisional application No. 61/439,913, filed on Feb. 6, 2011, provisional application No. 61/414,451, filed on Nov. 17, 2010, provisional application No. 61/388,002, filed on Sep. 30, 2010, provisional application No. 61/352,166, filed on Jun. 7, 2010.

(51) Int. Cl.

| | | |
|---|---|---|
| *G10L 17/00* | (2013.01) | |
| *B25J 11/00* | (2006.01) | |
| *A61B 5/00* | (2006.01) | |
| *A61B 5/16* | (2006.01) | |
| *G06N 3/08* | (2006.01) | |
| *G06V 40/16* | (2022.01) | |

(52) U.S. Cl.
CPC ............. *G06N 3/08* (2013.01); *G06V 40/168* (2022.01); *G06V 40/172* (2022.01); *G10L 17/00* (2013.01); *A61M 2021/0022* (2013.01); *A61M 2021/0027* (2013.01); *A61M 2021/0044* (2013.01); *A61M 2205/3303* (2013.01)

(58) Field of Classification Search
CPC .... A61M 2205/3303; A61M 2021/005; A61M 2021/0088; A61M 2205/332; A61M 2205/3368; A61M 2205/3553; A61M 2205/10; A61M 2205/3375; A61M 2205/3561; A61M 2205/3592; A61M 2205/505; A61M 2205/52; A61M 2205/59; A61M 2205/609; A61M 2230/06; A61M 2230/50; A61B 5/0077; A61B 5/165; B25J 11/0005; B25J 9/161; B25J 9/163; G06K 9/00268; G06K 9/00288; G06K 9/00302; G06K 9/4604; G06K 9/4642; G06N 3/08; G06N 3/0472; G06N 3/0481; G06N 3/088; G06N 5/003; G06N 20/10; G06N 20/20; G06N 3/008; G06N 3/0454; G06N 3/084; G10L 17/00; G10L 25/63; G06F 3/167; G05B 19/042; G16H 30/40; G16H 50/20; G16H 20/70; G02C 11/10
USPC ...................................................... 600/407
See application file for complete search history.

(56) References Cited

U.S. PATENT DOCUMENTS

| | | |
|---|---|---|
| 3,870,034 A | 3/1975 | James |
| 4,353,375 A | 10/1982 | Colburn et al. |
| 4,448,203 A | 5/1984 | Williamson et al. |
| 4,794,533 A | 12/1988 | Cohen |
| 4,807,642 A | 2/1989 | Brown |
| 4,817,628 A | 4/1989 | Zealear et al. |
| 4,950,069 A | 8/1990 | Hutchinson |

(56) References Cited

U.S. PATENT DOCUMENTS

| | | |
|---|---|---|
| 4,964,411 A | 10/1990 | Johnson et al. |
| 5,016,282 A | 5/1991 | Tomono et al. |
| 5,031,228 A | 7/1991 | Lu |
| 5,219,322 A | 6/1993 | Weathers |
| 5,247,938 A | 9/1993 | Silverstein et al. |
| 5,259,390 A | 11/1993 | Maclean |
| 5,507,291 A | 4/1996 | Stirbl et al. |
| 5,572,596 A | 11/1996 | Wildes et al. |
| 5,619,571 A | 4/1997 | Sandstorm et al. |
| 5,647,834 A | 7/1997 | Ron |
| 5,649,061 A | 7/1997 | Smyth |
| 5,663,900 A | 9/1997 | Bhandari et al. |
| 5,666,215 A | 9/1997 | Fredlund et al. |
| 5,725,472 A | 3/1998 | Weathers |
| 5,741,217 A | 4/1998 | Gero |
| 5,760,917 A | 6/1998 | Sheridan |
| 5,762,611 A | 6/1998 | Lewis et al. |
| 5,772,508 A | 6/1998 | Sugita et al. |
| 5,772,591 A | 6/1998 | Cram |
| 5,774,591 A | 6/1998 | Black et al. |
| 5,802,220 A | 9/1998 | Black et al. |
| 5,825,355 A | 10/1998 | Palmer et al. |
| 5,886,683 A | 3/1999 | Tognazzini et al. |
| 5,898,423 A | 4/1999 | Tognazzini et al. |
| 5,920,477 A | 7/1999 | Hoffberg et al. |
| 5,945,988 A | 8/1999 | Williams et al. |
| 5,959,621 A | 9/1999 | Nawaz et al. |
| 5,969,755 A | 10/1999 | Courtney |
| 5,983,129 A | 11/1999 | Cowan et al. |
| 5,987,415 A | 11/1999 | Breese et al. |
| 6,004,061 A | 12/1999 | Manico et al. |
| 6,004,312 A | 12/1999 | Finneran et al. |
| 6,008,817 A | 12/1999 | Gilmore, Jr. |
| 6,026,321 A | 2/2000 | Miyata et al. |
| 6,026,322 A | 2/2000 | Korenman et al. |
| 6,056,781 A | 5/2000 | Wassick et al. |
| 6,067,565 A | 5/2000 | Horvitz |
| 6,088,040 A | 7/2000 | Oda et al. |
| 6,091,334 A | 7/2000 | Galiana et al. |
| 6,099,319 A | 8/2000 | Zaltman et al. |
| 6,134,644 A | 10/2000 | Mayuzumi et al. |
| 6,182,098 B1 | 1/2001 | Selker |
| 6,185,534 B1 | 2/2001 | Breese et al. |
| 6,195,651 B1 | 2/2001 | Handel et al. |
| 6,212,502 B1 | 4/2001 | Ball et al. |
| 6,222,607 B1 | 4/2001 | Szajewski et al. |
| 6,309,342 B1 | 10/2001 | Blazey et al. |
| 6,327,580 B1 | 12/2001 | Pierce et al. |
| 6,349,290 B1 | 2/2002 | Horowitz et al. |
| 6,351,273 B1 | 2/2002 | Lemelson et al. |
| 6,437,758 B1 | 8/2002 | Nielsen et al. |
| 6,443,840 B2 | 9/2002 | Von Kohorn |
| 6,530,082 B1 | 3/2003 | Del Sesto et al. |
| 6,551,165 B2 | 4/2003 | Smirnov |
| 6,577,329 B1 | 6/2003 | Flickner et al. |
| 6,606,102 B1 | 8/2003 | Odom |
| 6,629,104 B1 | 9/2003 | Parulski et al. |
| 6,792,458 B1 | 9/2004 | Muret et al. |
| 6,847,376 B2 | 1/2005 | Engeldrum et al. |
| 7,003,135 B2 | 2/2006 | Hsieh et al. |
| 7,013,478 B1 | 3/2006 | Hendricks et al. |
| 7,113,916 B1 | 9/2006 | Hill |
| 7,120,880 B1 | 10/2006 | Dryer et al. |
| 7,197,459 B1 | 3/2007 | Harinarayan et al. |
| 7,233,684 B2 | 6/2007 | Fedorovskaya et al. |
| 7,246,081 B2 | 7/2007 | Hill |
| 7,263,474 B2 | 8/2007 | Fables et al. |
| 7,266,582 B2 | 9/2007 | Stelting |
| 7,307,636 B2 | 12/2007 | Matraszek et al. |
| 7,319,779 B1 | 1/2008 | Mummareddy et al. |
| 7,327,505 B2 | 2/2008 | Fedorovskaya et al. |
| 7,350,138 B1 | 3/2008 | Swaminathan et al. |
| 7,353,399 B2 | 4/2008 | Ooi et al. |
| 7,355,627 B2 | 4/2008 | Yamazaki et al. |
| 7,428,318 B1 | 9/2008 | Madsen et al. |
| 7,474,801 B2 | 1/2009 | Teo et al. |
| 7,496,622 B2 | 2/2009 | Brown et al. |
| 7,505,621 B1 | 3/2009 | Agrawal et al. |
| 7,549,161 B2 | 6/2009 | Poo et al. |
| 7,551,755 B1 | 6/2009 | Steinberg et al. |
| 7,555,148 B1 | 6/2009 | Steinberg et al. |
| 7,558,408 B1 | 7/2009 | Steinberg et al. |
| 7,564,994 B1 | 7/2009 | Steinberg et al. |
| 7,573,439 B2 | 8/2009 | Lau et al. |
| 7,580,512 B2 | 8/2009 | Batni et al. |
| 7,584,435 B2 | 9/2009 | Bailey et al. |
| 7,587,068 B1 | 9/2009 | Steinberg et al. |
| 7,610,289 B2 | 10/2009 | Muret et al. |
| 7,620,934 B2 | 11/2009 | Falter et al. |
| 7,644,375 B1 | 1/2010 | Anderson et al. |
| 7,676,574 B2 | 3/2010 | Glommen et al. |
| 7,757,171 B1 | 7/2010 | Wong et al. |
| 7,826,657 B2 | 11/2010 | Zhang et al. |
| 7,830,570 B2 | 11/2010 | Morita et al. |
| 7,881,493 B1 | 2/2011 | Edwards et al. |
| 7,921,036 B1 | 4/2011 | Sharma |
| 8,010,458 B2 | 8/2011 | Galbreath et al. |
| 8,022,831 B1 | 9/2011 | Wood-Eyre |
| 8,219,438 B1 | 7/2012 | Moon et al. |
| 8,401,248 B1 | 3/2013 | Moon et al. |
| 8,442,638 B2 | 5/2013 | Libbus et al. |
| 8,522,779 B2 | 9/2013 | Lee et al. |
| 8,600,120 B2 | 12/2013 | Gonion et al. |
| 8,640,021 B2 | 1/2014 | Perez et al. |
| 8,996,429 B1 * | 3/2015 | Francis, Jr. ........... G06F 16/214 706/12 |
| 10,424,318 B2 * | 9/2019 | Levy-Rosenthal ..... G10L 25/63 |
| 10,786,895 B2 * | 9/2020 | Lee ................. G06K 9/00664 |
| 10,832,118 B2 * | 11/2020 | Rakshit ............. G06K 9/00335 |
| 10,946,528 B2 * | 3/2021 | Gupta ............... B25J 11/0015 |
| 2001/0033286 A1 | 10/2001 | Stokes et al. |
| 2001/0041021 A1 | 11/2001 | Boyle et al. |
| 2002/0007249 A1 | 1/2002 | Cranley |
| 2002/0030665 A1 | 3/2002 | Ano |
| 2002/0042557 A1 | 4/2002 | Bensen et al. |
| 2002/0054174 A1 | 5/2002 | Abbott et al. |
| 2002/0084902 A1 | 7/2002 | Zadrozny et al. |
| 2002/0171551 A1 | 11/2002 | Eshelman |
| 2002/0182574 A1 | 12/2002 | Freer |
| 2003/0035567 A1 | 2/2003 | Chang et al. |
| 2003/0037041 A1 | 2/2003 | Hertz |
| 2003/0060728 A1 | 3/2003 | Mandigo |
| 2003/0093784 A1 | 5/2003 | Dimitrova et al. |
| 2003/0182123 A1 | 9/2003 | Mitsuyoshi |
| 2003/0191682 A1 | 10/2003 | Shepard et al. |
| 2003/0191816 A1 | 10/2003 | Landress et al. |
| 2004/0039483 A1 | 2/2004 | Kemp et al. |
| 2004/0181457 A1 | 9/2004 | Biebesheimer |
| 2005/0187437 A1 | 8/2005 | Matsugu |
| 2005/0283055 A1 | 12/2005 | Shirai et al. |
| 2005/0289582 A1 | 12/2005 | Tavares et al. |
| 2006/0019224 A1 | 1/2006 | Behar et al. |
| 2006/0143647 A1 | 6/2006 | Bill |
| 2006/0170945 A1 | 8/2006 | Bill |
| 2006/0235753 A1 | 10/2006 | Kameyama |
| 2007/0167689 A1 | 7/2007 | Ramadas et al. |
| 2007/0173733 A1 | 7/2007 | Le et al. |
| 2007/0239787 A1 | 10/2007 | Cunningham et al. |
| 2007/0255831 A1 | 11/2007 | Hayashi et al. |
| 2007/0265507 A1 | 11/2007 | de Lemos |
| 2007/0299964 A1 | 12/2007 | Wong et al. |
| 2008/0059570 A1 | 3/2008 | Bill |
| 2008/0091512 A1 | 4/2008 | Marci et al. |
| 2008/0091515 A1 | 4/2008 | Thieberger et al. |
| 2008/0101660 A1 | 5/2008 | Seo |
| 2008/0103784 A1 | 5/2008 | Wong et al. |
| 2008/0167757 A1 | 7/2008 | Kanevsky et al. |
| 2008/0184170 A1 | 7/2008 | Periyalwar |
| 2008/0201144 A1 | 8/2008 | Song et al. |
| 2008/0208015 A1 | 8/2008 | Morris et al. |
| 2008/0221472 A1 | 9/2008 | Lee et al. |
| 2008/0287821 A1 | 11/2008 | Jung et al. |
| 2008/0292151 A1 | 11/2008 | Kurtz et al. |
| 2009/0002178 A1 | 1/2009 | Guday et al. |

(56) References Cited

U.S. PATENT DOCUMENTS

| | | |
|---|---|---|
| 2009/0006206 A1 | 1/2009 | Groe |
| 2009/0083421 A1 | 3/2009 | Glommen et al. |
| 2009/0094286 A1 | 4/2009 | Lee et al. |
| 2009/0112694 A1 | 4/2009 | Jung et al. |
| 2009/0112810 A1 | 4/2009 | Jung et al. |
| 2009/0133048 A1 | 5/2009 | Gibbs et al. |
| 2009/0150919 A1 | 6/2009 | Lee et al. |
| 2009/0156907 A1 | 6/2009 | Jung et al. |
| 2009/0164132 A1 | 6/2009 | Jung et al. |
| 2009/0193344 A1 | 7/2009 | Smyers |
| 2009/0210290 A1 | 8/2009 | Elliott et al. |
| 2009/0217315 A1 | 8/2009 | Malik et al. |
| 2009/0259518 A1 | 10/2009 | Harvey |
| 2009/0270170 A1 | 10/2009 | Patton |
| 2009/0271417 A1 | 10/2009 | Toebes et al. |
| 2009/0285456 A1 | 11/2009 | Moon et al. |
| 2009/0299840 A1 | 12/2009 | Smith |
| 2010/0070523 A1 | 3/2010 | Delgo et al. |
| 2010/0086215 A1 | 4/2010 | Bartlett et al. |
| 2010/0099955 A1 | 4/2010 | Thomas et al. |
| 2010/0266213 A1 | 10/2010 | Hill |
| 2010/0274847 A1 | 10/2010 | Anderson et al. |
| 2010/0324437 A1 | 12/2010 | Freeman |
| 2011/0007174 A1 | 1/2011 | Bacivarov et al. |
| 2011/0126226 A1 | 5/2011 | Makhlouf |
| 2011/0134026 A1 | 6/2011 | Kang et al. |
| 2011/0143728 A1 | 6/2011 | Holopainen et al. |
| 2011/0144971 A1 | 6/2011 | Danielson |
| 2011/0196855 A1 | 8/2011 | Wable et al. |
| 2011/0231240 A1 | 9/2011 | Schoen et al. |
| 2011/0251493 A1 | 10/2011 | Poh et al. |
| 2011/0263946 A1 | 10/2011 | el Kaliouby et al. |
| 2012/0271484 A1 | 10/2012 | Feit et al. |
| 2012/0324491 A1 | 12/2012 | Bathiche et al. |
| 2013/0023337 A1 | 1/2013 | Bowers et al. |
| 2013/0116587 A1 | 5/2013 | Sommo et al. |
| 2013/0197409 A1 | 8/2013 | Baxter et al. |
| 2014/0172910 A1 | 6/2014 | Jung et al. |
| 2016/0104486 A1 | 4/2016 | Penilla et al. |
| 2017/0003784 A1 | 1/2017 | Garg et al. |
| 2018/0050696 A1 | 2/2018 | Misu et al. |
| 2018/0114125 A1* | 4/2018 | Ichiboshi ............ A61B 5/0077 |
| 2018/0251122 A1 | 9/2018 | Golston et al. |
| 2019/0135325 A1 | 5/2019 | Lisseman et al. |
| 2019/0164548 A1* | 5/2019 | Yoon ....................... G10L 15/22 |
| 2020/0005787 A1* | 1/2020 | Shin ........................ G06F 3/167 |
| 2020/0171977 A1 | 6/2020 | Jales Costa et al. |
| 2020/0223362 A1 | 7/2020 | Witte |
| 2020/0285871 A1 | 9/2020 | Tokizaki et al. |
| 2020/0130528 A1 | 10/2020 | Upmanue et al. |

FOREIGN PATENT DOCUMENTS

| | | |
|---|---|---|
| KR | 10-2008-0016303 A | 2/2008 |
| KR | 1020100048688 A | 5/2010 |
| WO | WO 2011/045422 A1 | 4/2011 |

OTHER PUBLICATIONS

International Search Report dated Nov. 14, 2011 for PCT/US2011/39282.

International Search Report dated Apr. 16, 2012 for PCT/US2011/054125.

International Search Report dated May 24, 2012 for PCT/US2011/060900.

Xiaoyu Wang, An HOG-LBP human detector with partial occlusion handling, Sep. 29, 2009, IEEE 12th International Conference on Computer Vision, Kyoto, Japan.

Zhihong Zeng, A Survey of Affect Recognition Methods: Audio, Visual, and Spontaneous Expressions, Jan. 2009, IEEE Transactions on Pattern Analysis and Machine Intelligence, vol. 31, No. 1.

Nicholas R. Howe and Amanda Ricketson, Improving the Boosted Correlogram, 2004, Lecture Notes in Computer Science, ISSN 0302-9743, Springer-Verlag, Germany.

Xuming He, et al., Learning and Incorporating Top-Down Cues in Image Segmentation, 2006, Lecture Notes in Computer Science, ISBN 978-3-540-33832-1, Springer-Verlag, Germany.

Ross Eaton, et al., Rapid Training of Image Classifiers through Adaptive, Multi-frame Sampling Methods, Oct. 2008, IEEE 37th Applied Imagery Pattern Recognition Workshop, Washington DC.

Verkruysse, Wim, Lars O. Svaasand, and J. Stuart Nelson. "Remote plethysmographic imaging using ambient light." Optics express 16.26 (2008): 21434-21445.

Albiol, Alberto, et al. "Face recognition using HOG-EBGM." Pattern Recognition Letters 29.10 (2008): 1537-1543.

Fasel, B. (Aug. 2002). Robust face analysis using convolutional neural networks. In Object recognition supported by user interaction for service robots (vol. 2, pp. 40-43). IEEE.

Matsugu, M., Mori, K., Mitari, Y., & Kaneda, Y. (2003). Subject independent facial expression recognition with robust face detection using a convolutional neural network. Neural Networks, 16(5-6), 555-559.

\* cited by examiner

ROBOTIC CONTROL USING PROFILES

RELATED APPLICATIONS

This application claims the benefit of U.S. provisional patent applications "Vehicle Interior Object Management" Ser. No. 62/893,298, filed Aug. 29, 2019, "Deep Learning In Situ Retraining" Ser. No. 62/925,990, filed Oct. 25, 2019, "Data Versioning for Neural Network Training" Ser. No. 62/926,009, filed Oct. 25, 2019, "Synthetic Data Augmentation for Neural Network Training" Ser. No. 62/954,819, filed Dec. 30, 2019, "Synthetic Data for Neural Network Training Using Vectors" Ser. No. 62/954,833, filed Dec. 30, 2019, and "Autonomous Vehicle Control Using Longitudinal Profile Generation" Ser. No. 62/955,493, filed Dec. 31, 2019.

This application is also a continuation-in-part of U.S. patent application "Robot Navigation for Personal Assistance" Ser. No. 16/781,334, filed Feb. 4, 2020, which claims the benefit of U.S. provisional patent applications "Synthetic Data Augmentation for Neural Network Training" Ser. No. 62/954,819, filed Dec. 30, 2019, "Synthetic Data for Neural Network Training Using Vectors" Ser. No. 62/954,833, filed Dec. 30, 2019, and "Autonomous Vehicle Control Using Longitudinal Profile Generation" Ser. No. 62/955,493, filed Dec. 31, 2019.

The U.S. patent application "Robot Navigation for Personal Assistance" Ser. No. 16/781,334, filed Feb. 4, 2020 is a continuation-in-part of U.S. patent application "Electronic Display Viewing Verification" Ser. No. 16/726,647, filed Dec. 24, 2019, which claims the benefit of U.S. provisional patent applications "Image Analysis for Human Perception Artificial Intelligence" Ser. No. 62/827,088, filed Mar. 31, 2019, "Vehicle Interior Object Management" Ser. No. 62/893,298, filed Aug. 29, 2019, "Deep Learning In Situ Retraining" Ser. No. 62/925,990, filed Oct. 25, 2019, and "Data Versioning for Neural Network Training" Ser. No. 62/926,009, filed Oct. 25, 2019.

The U.S. patent application "Electronic Display Viewing Verification" Ser. No. 16/726,647, filed Dec. 24, 2019, is also a continuation-in-part of U.S. patent application "Facial Tracking With Classifiers For Query Evaluation" Ser. No. 16/146,194, filed Sep. 28, 2018, which claims the benefit of U.S. provisional patent applications "Speech Analysis for Cross-Language Mental State Identification" Ser. No. 62/593,449, filed Dec. 1, 2017, "Avatar Image Animation using Translation Vectors" Ser. No. 62/593,440, filed Dec. 1, 2017, "Directed Control Transfer for Autonomous Vehicles" Ser. No. 62/611,780, filed Dec. 29, 2017, "Cognitive State Vehicle Navigation Based on Image Processing" Ser. No. 62/625,274, filed Feb. 1, 2018, "Cognitive State Based Vehicle Manipulation Using Near Infrared Image Processing" Ser. No. 62/637,567, filed Mar. 2, 2018, and "Vehicle Manipulation Using Cognitive State" Ser. No. 62/679,825, filed Jun. 3, 2018.

The U.S. patent application "Facial Tracking With Classifiers For Query Evaluation" Ser. No. 16/146,194, filed Sep. 28, 2018 is also a continuation-in-part of U.S. patent application "Facial Tracking with Classifiers" Ser. No. 14/848,222, filed Sep. 8, 2015 which claims the benefit of U.S. provisional patent applications "Facial Tracking with Classifiers" Ser. No. 62/047,508, filed Sep. 8, 2014, "Semiconductor Based Mental State Analysis" Ser. No. 62/082,579, filed Nov. 20, 2014, and "Viewership Analysis Based on Facial Evaluation" Ser. No. 62/128,974, filed Mar. 5, 2015.

The U.S. patent application "Facial Tracking with Classifiers" Ser. No. 14/848,222, filed Sep. 8, 2015 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

The U.S. patent application "Facial Tracking with Classifiers" Ser. No. 14/848,222, filed Sep. 8, 2015 is also a continuation-in-part of U.S. patent application "Mental State Analysis Using an Application Programming Interface" Ser. No. 14/460,915, Aug. 15, 2014, which claims the benefit of U.S. provisional patent applications "Application Programming Interface for Mental State Analysis" Ser. No. 61/867,007, filed Aug. 16, 2013, "Mental State Analysis Using an Application Programming Interface" Ser. No. 61/924,252, filed Jan. 7, 2014, "Heart Rate Variability Evaluation for Mental State Analysis" Ser. No. 61/916,190, filed Dec. 14, 2013, "Mental State Analysis for Norm Generation" Ser. No. 61/927,481, filed Jan. 15, 2014, "Expression Analysis in Response to Mental State Express Request" Ser. No. 61/953,878, filed Mar. 16, 2014, "Background Analysis of Mental State Expressions" Ser. No. 61/972,314, filed Mar. 30, 2014, and "Mental State Event Definition Generation" Ser. No. 62/023,800, filed Jul. 11, 2014.

The U.S. patent application "Mental State Analysis Using an Application Programming Interface" Ser. No. 14/460,915, Aug. 15, 2014 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

The U.S. patent application "Facial Tracking With Classifiers For Query Evaluation" Ser. No. 16/146,194, filed Sep. 28, 2018 is also a continuation-in-part of U.S. patent application "Image Analysis for Attendance Query Evaluation" Ser. No. 15/061,385, filed Mar. 4, 2016, which claims the benefit of U.S. provisional patent applications "Viewership Analysis Based on Facial Evaluation" Ser. No. 62/128,974, filed Mar. 5, 2015, "Mental State Event Signature Usage" Ser. No. 62/217,872, filed Sep. 12, 2015, "Image Analysis In Support of Robotic Manipulation" Ser. No. 62/222,518, filed Sep. 23, 2015, "Analysis of Image Content with Associated Manipulation of Expression Presentation" Ser. No. 62/265,937, filed Dec. 12, 2015, "Image Analysis Using Sub-Sectional Component Evaluation To Augment Classifier Usage" Ser. No. 62/273,896, filed Dec. 31, 2015, and "Analytics for Live Streaming Based on Image Analysis within a Shared Digital Environment" Ser. No. 62/301,558, filed Feb. 29, 2016.

The U.S. patent application "Image Analysis for Attendance Query Evaluation" Ser. No. 15/061,385, filed Mar. 4, 2016 is also a continuation-in-part of U.S. patent application "Facial Tracking with Classifiers" Ser. No. 14/848,222, filed Sep. 8, 2015 which claims the benefit of U.S. provisional patent applications "Facial Tracking with Classifiers" Ser. No. 62/047,508, filed Sep. 8, 2014, "Semiconductor Based Mental State Analysis" Ser. No. 62/082,579, filed Nov. 20, 2014, and "Viewership Analysis Based On Facial Evaluation" Ser. No. 62/128,974, filed Mar. 5, 2015.

The U.S. patent application "Image Analysis for Attendance Query Evaluation" Ser. No. 15/061,385, filed Mar. 4, 2016 is also a continuation-in-part of U.S. patent application "Measuring Affective Data for Web-Enabled Applications" Ser. No. 13/249,317, filed Sep. 30, 2011 which claims the benefit of U.S. provisional patent applications "Measuring Affective Data for Web-Enabled Applications" Ser. No. 61/388,002, filed Sep. 30, 2010, "Sharing Affect Data Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

The U.S. patent application "Robot Navigation for Personal Assistance" Ser. No. 16/781,334, filed Feb. 4, 2020 is also a continuation-in-part of U.S. patent application "Image Analysis In Support Of Robotic Manipulation" Ser. No. 15/273,765, filed Sep. 23, 2016, which claims the benefit of U.S. provisional patent applications "Image Analysis In Support of Robotic Manipulation" Ser. No. 62/222,518, filed Sep. 23, 2015, "Analysis of Image Content with Associated Manipulation of Expression Presentation" Ser. No. 62/265,937, filed Dec. 12, 2015, "Image Analysis Using Sub-Sectional Component Evaluation To Augment Classifier Usage" Ser. No. 62/273,896, filed Dec. 31, 2015, "Analytics for Live Streaming Based on Image Analysis within a Shared Digital Environment" Ser. No. 62/301,558, filed Feb. 29, 2016, and "Deep Convolutional Neural Network Analysis of Images for Mental States" Ser. No. 62/370,421, filed Aug. 3, 2016.

The U.S. patent application "Image Analysis In Support Of Robotic Manipulation" Ser. No. 15/273,765, filed Sep. 23, 2016, is also a continuation-in-part of U.S. patent application "Mental State Event Definition Generation" Ser. No. 14/796,419, filed Jul. 10, 2015 which claims the benefit of U.S. provisional patent applications "Mental State Event Definition Generation" Ser. No. 62/023,800, filed Jul. 11, 2014, "Facial Tracking with Classifiers" Ser. No. 62/047,508, filed Sep. 8, 2014, "Semiconductor Based Mental State Analysis" Ser. No. 62/082,579, filed Nov. 20, 2014, and "Viewership Analysis Based On Facial Evaluation" Ser. No. 62/128,974, filed Mar. 5, 2015.

The U.S. patent application "Mental State Event Definition Generation" Ser. No. 14/796,419, filed Jul. 10, 2015 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

The U.S. patent application "Mental State Event Definition Generation" Ser. No. 14/796,419, filed Jul. 10, 2015 is also a continuation-in-part of U.S. patent application "Mental State Analysis Using an Application Programming Interface" Ser. No. 14/460,915, Aug. 15, 2014, which claims the benefit of U.S. provisional patent applications "Application Programming Interface for Mental State Analysis" Ser. No. 61/867,007, filed Aug. 16, 2013, "Mental State Analysis Using an Application Programming Interface" Ser. No. 61/924,252, filed Jan. 7, 2014, "Heart Rate Variability Evaluation for Mental State Analysis" Ser. No. 61/916,190, filed Dec. 14, 2013, "Mental State Analysis for Norm Generation" Ser. No. 61/927,481, filed Jan. 15, 2014, "Expression Analysis in Response to Mental State Express Request" Ser. No. 61/953,878, filed Mar. 16, 2014, "Background Analysis of Mental State Expressions" Ser. No. 61/972,314, filed Mar. 30, 2014, and "Mental State Event Definition Generation" Ser. No. 62/023,800, filed Jul. 11, 2014.

The U.S. patent application "Mental State Event Definition Generation" Ser. No. 14/796,419, filed Jul. 10, 2015 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

This application is also a continuation-in-part of U.S. patent application "Smart Toy Interaction using Image Analysis" Ser. No. 15/861,866, filed Jan. 4, 2018, which claims the benefit of U.S. provisional patent applications "Smart Toy Interaction using Image Analysis" Ser. No. 62/442,291, filed Jan. 4, 2017, "Audio Analysis Learning using Video Data" Ser. No. 62/442,325, filed Jan. 4, 2017, "Vehicle Manipulation using Occupant Image Analysis" Ser. No. 62/448,448, filed Jan. 20, 2017, "Image Analysis for Two-sided Data Hub" Ser. No. 62/469,591, filed Mar. 10, 2017, "Vehicle Artificial Intelligence Evaluation of Mental States" Ser. No. 62/503,485, filed May 9, 2017, "Image Analysis for Emotional Metric Generation" Ser. No. 62/524,606, filed Jun. 25, 2017, "Image Analysis and Representation for Emotional Metric Threshold Evaluation" Ser. No. 62/541,847, filed Aug. 7, 2017, "Multimodal Machine Learning for Emotion Metrics" Ser. No. 62/557,460, filed Sep. 12, 2017, "Speech Analysis for Cross-Language Mental State Identification" Ser. No. 62/593,449, filed Dec. 1, 2017, "Avatar Image Animation using Translation Vectors" Ser. No. 62/593,440, filed Dec. 1, 2017, and "Directed Control Transfer for Autonomous Vehicles" Ser. No. 62/611,780, filed Dec. 29, 2017.

The U.S. patent application "Smart Toy Interaction Using Image Analysis" Ser. No. 15/861,866, filed Jan. 4, 2018 is also a continuation-in-part of U.S. patent application "Image Analysis in Support of Robotic Manipulation" Ser. No. 15/273,765, filed Sep. 23, 2016, which claims the benefit of U.S. provisional patent applications "Image Analysis In Support of Robotic Manipulation" Ser. No. 62/222,518, filed Sep. 23, 2015, "Analysis of Image Content with Associated Manipulation of Expression Presentation" Ser. No. 62/265,937, filed Dec. 12, 2015, "Image Analysis Using Sub-Sectional Component Evaluation To Augment Classifier Usage" Ser. No. 62/273,896, filed Dec. 31, 2015, "Analytics for Live Streaming Based on Image Analysis within a Shared Digital Environment" Ser. No. 62/301,558, filed Feb. 29, 2016, and "Deep Convolutional Neural Network Analysis of Images for Mental States" Ser. No. 62/370,421, filed Aug. 3, 2016.

The U.S. patent application "Image Analysis in Support of Robotic Manipulation" Ser. No. 15/273,765, filed Sep. 23, 2016 is a continuation-in-part of U.S. patent application "Mental State Event Definition Generation" Ser. No. 14/796,419, filed Jul. 10, 2015 which claims the benefit of U.S. provisional patent applications "Mental State Event Definition Generation" Ser. No. 62/023,800, filed Jul. 11, 2014, "Facial Tracking with Classifiers" Ser. No. 62/047,508, filed Sep. 8, 2014, "Semiconductor Based Mental State Analysis" Ser. No. 62/082,579, filed Nov. 20, 2014, and "Viewership Analysis Based On Facial Evaluation" Ser. No. 62/128,974, filed Mar. 5, 2015.

The U.S. patent application "Mental State Event Definition Generation" Ser. No. 14/796,419, filed Jul. 10, 2015 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

The U.S. patent application "Mental State Event Definition Generation" Ser. No. 14/796,419, filed Jul. 10, 2015 is also a continuation-in-part of U.S. patent application "Mental State Analysis Using an Application Programming Interface" Ser. No. 14/460,915, Aug. 15, 2014, which claims the benefit of U.S. provisional patent applications "Application Programming Interface for Mental State Analysis" Ser. No. 61/867,007, filed Aug. 16, 2013, "Mental State Analysis Using an Application Programming Interface" Ser. No. 61/924,252, filed Jan. 7, 2014, "Heart Rate Variability Evaluation for Mental State Analysis" Ser. No. 61/916,190, filed Dec. 14, 2013, "Mental State Analysis for Norm Generation" Ser. No. 61/927,481, filed Jan. 15, 2014, "Expression Analysis in Response to Mental State Express Request" Ser. No. 61/953,878, filed Mar. 16, 2014, "Background Analysis of Mental State Expressions" Ser. No. 61/972,314, filed Mar. 30, 2014, and "Mental State Event Definition Generation" Ser. No. 62/023,800, filed Jul. 11, 2014.

The U.S. patent application "Mental State Event Definition Generation" Ser. No. 14/796,419, filed Jul. 10, 2015 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

Each of the foregoing applications is hereby incorporated by reference in its entirety.

FIELD OF ART

This application relates generally to robotic control, and more particularly to robotic control using profiles.

BACKGROUND

Robots, and automata before them, have fascinated, amused, and served the people who interact with them. The designs of these devices have evolved from the mechanical amusements and wonders such as Vaucanson's Canard Digérateur (Digesting Duck), to the computer-controlled machines that are used for manufacturing, bomb disposal, and tackling dummies. Other robots enhance the capabilities of the person interacting with the robot. A collaborative robot or "cobot" enables the person using it to reach farther, lift greater weights, and work in environments which are dangerous or lethal to humans, among other capabilities. In some situations, cobots can be operated remotely to perform critical tasks including remote surgery.

Robots have long been used to perform useful tasks in a variety of platforms. Some robots are designed for only one function, such as welding robots used in an automobile manufacturing assembly line. This type of robot is designed to perform a repetitive task in potentially harsh environments and is not tied to operating on a particular schedule. As such, welding robots can be productive components of a manufacturing system. There are different kinds of robots that are able to perform multiple tasks, and some can even be reprogrammed to perform new tasks. Robots are becoming more and more prevalent in society. At one time, robots, like the welding robot previously described, were primarily used in factories where conditions were conducive to repetitive motions in harsh environments. However, today's robots are much more sophisticated and are no longer only found in unfriendly manufacturing buildings. For example, robots are now able to self-navigate around a house in order to perform household vacuuming. As robots become more common in society, they are emerging as candidates for many tasks that were once reserved only for humans.

SUMMARY

Techniques for robotic control using profiles are disclosed. Cognitive state data for an individual is obtained. A cognitive state profile for the individual is learned using the cognitive state data that was obtained. Further cognitive state data for the individual is collected. The further cognitive state data is compared with the cognitive state profile. Stimuli are provided by a robot to the individual based on the comparing. The robot can be a smart toy. The cognitive state data can include facial image data for the individual. The further cognitive state data can include audio data for the individual. The audio data can be voice data. The voice data augments the cognitive state data. Cognitive state data for the individual is obtained using another robot. The cognitive state profile is updated based on input from either of the robots.

The cognitive state profile for the individual is based on image classifiers that are used with the cognitive state data. The cognitive state profile is initialized based on demographic data obtained from the individual. The learning the cognitive state profile includes augmenting an existing cognitive state profile based on the cognitive state data that was obtained. The cognitive state profile includes use patterns for the first robot. The cognitive state profile includes information on usage time for the first robot. Further cognitive state data is collected from the individual. The further collecting includes collecting voice data and augmenting the cognitive state data with the voice data. The further collecting includes collecting, by the first robot, temperature of the individual, heart rate information for the individual, or accelerometer data for the first robot. The further collecting includes collecting, by the first robot, physiological information for the individual.

The further cognitive state data is compared with the cognitive state profile. The comparing can confirm accuracy of the profile, and can identify variations in the profile or deviations from the profile. The comparing can be used for the learning of the cognitive state profile. Stimuli are provided by a first robot to the individual based on the comparing. The providing stimuli can include providing positive reinforcement for an educational effort. The providing stimuli can include visual stimuli, auditory stimuli, or haptic stimuli. The stimuli can include visual stimuli, such as images and text on a screen, lights, flashes, and so on. The stimuli can include auditory stimuli such as music, a voice, sound effects, alarms, etc. The stimuli can include haptic stimuli such as shakes, vibrations, force feedback, and so on. The stimuli can be used for the learning the cognitive state profile. The learning is accomplished on the first robot with stimuli being provided by the second robot. The stimuli being provided by the second robot are based on the learning on the first robot.

A processor-implemented method for robotic control is disclosed comprising: obtaining, using a first computing device, cognitive state data for an individual including facial data for the individual; learning, using a second computing device, a cognitive state profile for the individual using the cognitive state data that was obtained; collecting further cognitive state data for the individual; comparing the further cognitive state data with the cognitive state profile; and providing stimuli by a first robot to the individual based on the comparing.

Various features, aspects, and advantages of various embodiments will become more apparent from the following further description.

BRIEF DESCRIPTION OF THE DRAWINGS

The following detailed description of certain embodiments may be understood by reference to the following figures wherein.

DETAILED DESCRIPTION

Figure 1:
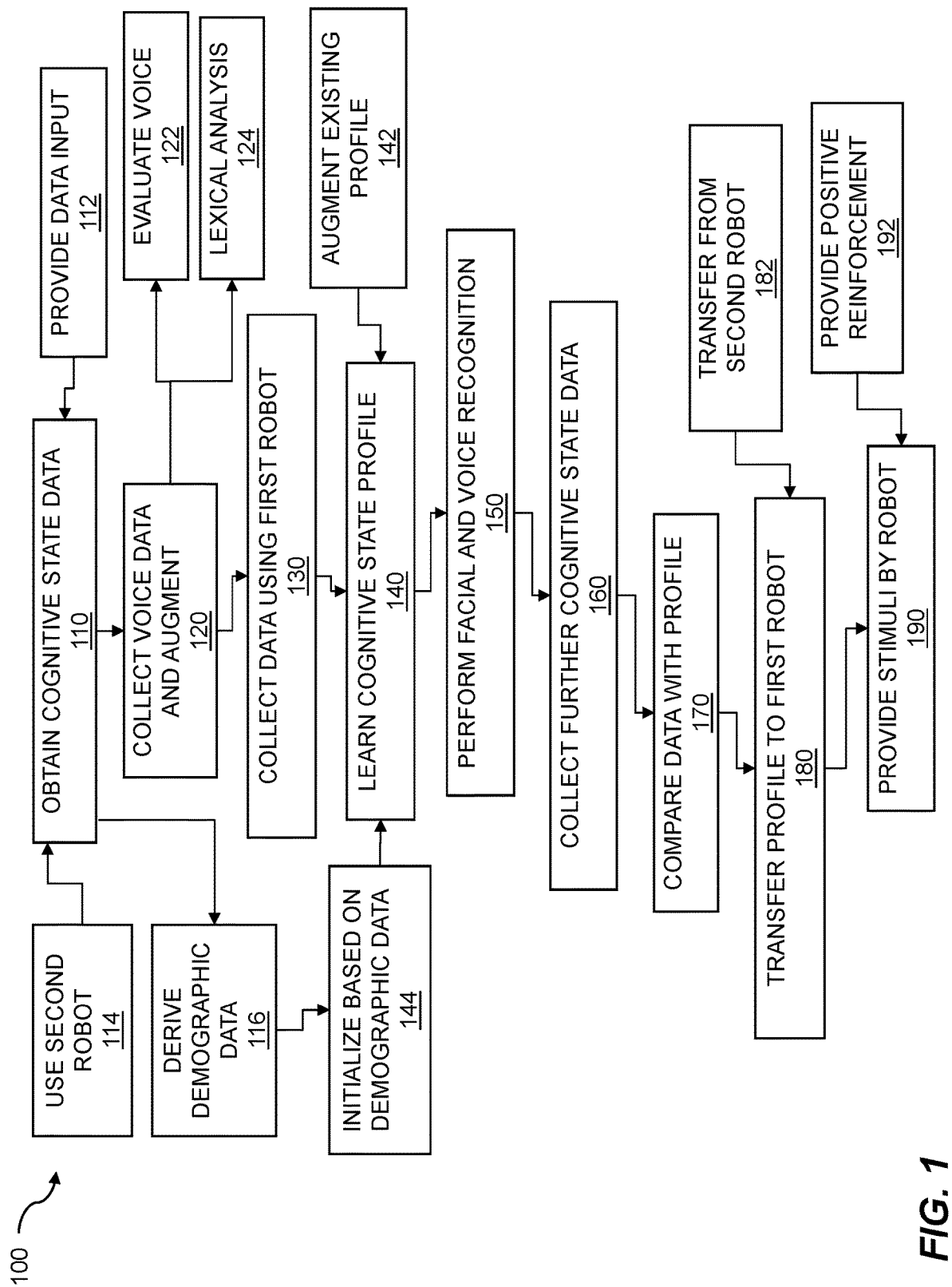
FIG. 1 is a flow diagram for robot interaction.

Humans engage in play for many purposes including pleasure, entertainment, relaxation, amusement, physical activity, and so on. Play can positively influence creativity, cognitive ability, physical ability, and social interaction. Some forms of play include interacting with a "toy". A toy can be an improvised toy such as a round pebble, a stick, or a tuna can. A toy can be a traditional plaything such as a doll, a plush animal, or a vehicle. More recently, a toy can be a video game console, a computer, a drone, or even a humanoid robot or a robotic pet. Notwithstanding the form of play in which humans choose to participate, those humans can directly benefit from their playtime activities.

However, toys historically have had no ability to respond interactively and autonomously to the person using the toy. Therefore, a need exists for interactive and autonomous toy response to increase play enjoyment, value, and interest. Toys have been used for many purposes other than simply for play. Some toys have been used for educational purposes such as models of bodies and engines, construction toys, and so on. Other toys have been used for social purposes such as a plush animal given to a child in a crisis or a robotic toy seal given to a dementia patient. The toys can be used to train, comfort, monitor, and engage. An individual can be observed as she or he interacts with a toy. The observation of the individual can be used for a variety of purposes including gauging how the individual interacts with the toy. Such interaction can promote educational purposes, social purposes, therapeutic purposes, etc.

In disclosed techniques, profiles are used for robotic control. Cognitive state data for an individual is obtained. A cognitive state profile for the individual is learned using the cognitive state data that was obtained. Further cognitive state data for the individual is collected. The further cognitive state data is compared with the cognitive state profile. Stimuli are provided by a robot to the individual based on the comparing. The robot can be a smart toy. The cognitive state data can include facial image data for the individual. The further cognitive state data can include audio data for the individual. The audio data can be voice data. The voice data augments the cognitive state data. Cognitive state data for the individual is obtained using another robot. The cognitive state profile is updated based on input from either of the robots. The cognitive state profile can be based on cognitive state event temporal signatures, on classifiers, on demographic information, or on an existing cognitive state profile. The cognitive state profile can include use patterns for a robot. Further cognitive state data is collected for the individual. The further cognitive state data can include further facial data and audio data. The further cognitive state data is compared with the cognitive state profile. The comparing can augment the cognitive state profile, modify the cognitive state profile, and so on. Stimuli are provided to the individual by a first robot based on the comparing. The providing stimuli can include providing positive reinforcement for an educational effort. The providing stimuli can include visual, auditory, and haptic stimuli. The stimuli can include maneuvering a toy such as a drone (airplane, helicopter, car, truck, etc.).

A second robot can be used to augment, enhance, modify, or override the robot interaction provided, or intended, by the first robot. The second robot can be used to obtain the further cognitive state data. The second robot can be used to provide stimuli in response to the further cognitive state data. The second robot can be used to augment or update the cognitive state profile. The first and/or the second robot can be in the form of a smart toy robot, that is, a toy with embedded robotic functionality. The robotic functionality of the smart toy can take many different forms, for example, a toy, a pet, a butler, or an educational humanoid device, to name just a few.

The second robot can be substantially the same robot as the first robot or can be a different robot. A second robot substantially the same as the first robot may be a second doll or a second stuffed animal, for example, with either the exact same appearance and/or function or a similar appearance and/or function. Alternatively, a second robot smart toy that is different from the first robot smart toy may be an entirely different type of toy such as a second toy truck compared to a first toy doll. In this case, there is no confusion, even in the mind of a young child, that the toys are not the same. For example, a young child would generally not confuse a robotic smart ball toy with a smart toy stuffed animal. On the other hand, a young child may confuse a smart toy baby doll with a smart toy stuffed animal baby with a humanoid-shape.

FIG. 1 is a flow diagram for robot interaction. Interaction with a robot can be based on a profile. Profiles can be used for robotic control. Cognitive state data for an individual is obtained. A cognitive state profile for the individual is learned using the cognitive state data that was obtained. Further cognitive state data for the individual is collected. The further cognitive state data is compared with the cognitive state profile. Stimuli are provided by a robot to the individual based on the comparing. The providing stimuli can include visual stimuli, auditory stimuli, haptic stimuli, kinesthetic stimuli, and so on.

The flow 100 includes obtaining, using a first computing device, cognitive state data 110 for an individual including facial data for the individual. The cognitive state data can include voice data. In embodiments, the individual is a child, a teen, a young adult, an adult, a student, a patient, and so on. The obtaining cognitive state data can be based on a variety of techniques. In embodiments, the obtaining cognitive state data can be based on using one or more cameras to capture images of the individual. The images can contain the facial data. The camera or cameras can include a webcam, where a webcam can include a video camera, a still camera, a thermal imager, a CCD device, a phone camera, a three-dimensional camera, a depth camera, a light field (plenoptic) camera, multiple webcams used to show different views of a person, or any other type of image capture apparatus that can allow captured data to be used in an electronic system. In embodiments, the facial data for the individual can be obtained from a camera outside of the robot. The camera can be coupled to an electronic device such as a computer, a laptop computer, a tablet computer, a personal digital assistant, a smartphone, and so on. In other embodiments, the obtaining of the cognitive state data can be accomplished using a camera in a room occupied by the individual. A camera in a room with the individual can be placed on a piece of furniture, mounted on a wall or ceiling, and so on. In other embodiments, the facial data can be obtained from a camera inside of the robot. In embodiments, the obtaining cognitive state data includes voice data. The voice data can be obtained using a microphone or other audio capture technique.

Cognitive state data can be obtained using other techniques. In embodiments, the obtaining the cognitive state data is accomplished by one or more people providing data input 112 about the individual. The one or more people who may provide the cognitive state data can include a parent, an educator, an advisor, a clinician, a caregiver, and so on. Another technique for obtaining cognitive state data can include uploading cognitive state data, downloading cognitive state data, etc. In embodiments, the cognitive state data is obtained from a repository of cognitive state information for the individual. Other apparatus can be used for capturing cognitive state data. In embodiments, the obtaining cognitive state data for the individual is accomplished using a second robot 114. The second robot, like the first robot, can be a teddy bear, a doll, an action figure, a vehicle, a plush toy, a robotic humanoid, a robotic pet, and so on. Embodiments include deriving demographic data 116 from the facial data. The demographic data can include age, gender, race, and ethnicity. The demographic data can include other information relating to the individual including educational level, household income, geographic location, and the like. The latter demographic information examples can be obtained by the one or more people providing the data input about the individual.

The flow 100 includes collecting voice data and augmenting 120 the cognitive state data with the voice data. The voice data and the cognitive state data can correspond to the individual. In embodiments, the voice data includes audio data. The voice data can be collected from the individual who is interacting with the robot, from another person such as a teacher or a caregiver who is in the room with the individual or observing the individual, and so on. The voice data can include audio data such as ambient room sounds, physiological sounds such as breathing, vocalizations, and so on. In embodiments, the audio data can provide context for the first robot. The context for the first robot can include whether the first robot is in use, whether another robot is in use, and so on. The voice data can be analyzed. In embodiments, the voice data can be evaluated 122 for timbre, prosody, vocal register, vocal resonance, pitch, loudness, speech rate, or language content. The analyzing the voice data can determine one or more cognitive states. The augmenting the cognitive state data can be based on lexical analysis 124 of the voice data that evaluates sentiment. The lexical analysis can be based on converting voice data to text and analyzing the text for keywords, key phrases, syntax, semantics, and so on. The lexical analysis of the voice data can assess sentiment of the individual.

The flow 100 includes collecting data using the first robot 130. The data that is collected can include data from the individual, environmental data, and other contextual data regarding the interaction of the individual with the first robot. In embodiments, collecting, by the first robot, includes collecting temperature of the individual, heart rate information for the individual, or accelerometer data for the first robot. In other embodiments, collecting, by the first robot, includes collecting physiological information for the individual. The physiological information can include eye blink rate, gaze direction, skin resistance, heart rate variability, and so on. In embodiments, the obtaining cognitive state data for the individual is accomplished using a second robot.

The flow 100 includes learning, using a second computing device, a cognitive state profile 140 for the individual using the cognitive state data that was obtained. Various techniques can be applied to the learning. In embodiments, the learning the cognitive state profile can be based on image classifiers used with the cognitive state data. The classifiers can be uploaded by an operator such as a parent, a teacher, or a caregiver, downloaded from the Internet, and so on. In embodiments, the cognitive state profile is initialized based on demographic data 144. The demographic data can be based on the demographic data derived from the facial data for the individual, demographic data input by the one or more people providing data including demographic data about the individual, etc. The cognitive state profile can be used to control the robot, configure the robot, etc., in order to improve the interaction between the individual and the robot. The demographic data that is derived can be augmented by setup parameters of the first robot. In embodiments, the learning of the cognitive state profile can include augmenting 142 an existing cognitive state profile based on the cognitive state data that was obtained. The augmenting can be based on voice data, audio data, and so on. The existing cognitive state profile can be uploaded by an operator such as a parent, educator, or caregiver; downloaded from the Internet; and so on. The cognitive state profile can be dependent upon a variety of factors, variables, and parameters. In embodiments, the cognitive state profile includes augmenting an existing cognitive state profile based on the cognitive state data that was obtained. The augmentation of the cognitive state profile can include other techniques. The cognitive state profile can include parameters, values, etc., that can be related to the smart toy. In embodiments, the cognitive state profile can include use patterns for the first robot. The use patterns can be related to time of day, day of week, day of month, and so on. In embodiments, the profile includes information on usage time for the first robot. Further techniques can be used to augment the cognitive state profile. In embodiments, the cognitive state profile is further learned based on input from a first robot and a second robot. The second robot can be the same type of toy as the first robot, or can be a different type of toy. In embodiments, the first robot and the second robot have disparate toy functions. The first robot and the second robot can have different numbers of cameras, microphones, numbers and types of sensors, etc. In embodiments, the first robot and the second robot have disparate toy appearances. The first robot smart toy can be a teddy bear, the second robot smart toy can be a toy truck, etc. In embodiments, the learning is accomplished on the first robot with stimuli being provided by the second robot. The stimuli provided by the second robot can include visual stimuli, auditory stimuli, haptic stimuli, and so on. In embodiments, the stimuli being provided by the second robot are based on the learning on the first robot.

The flow 100 includes performing both facial recognition and voice recognition 150 for the individual. The voice recognition can be based on voice features, voice characteristics, etc. The voice recognition can be based on using classifiers. The flow 100 includes collecting further cognitive state data 160 for the individual. The further cognitive state data can include further facial data for the individual. The further cognitive state data can be based on collected physiological data, temperature data, heart rate information, etc. The further data can include audio data for the individual, voice data for the individual or another person (e.g. a parent, an educator, or a caregiver), and so on. The further cognitive state data can be provided using a second robot. The further data can be obtained from a repository of cognitive state information for the individual, provided by one or more people such as a parent, educator, or caregiver, and so on. The flow 100 includes comparing the further cognitive state data with the cognitive state profile 170. The comparing can be used to determine whether the existing cognitive state profile should be augmented, adjusted, or adapted. The comparing can be used to measure educational or therapeutic progress, to find anomalies in the cognitive state data, and so on.

The flow 100 includes transferring the cognitive state profile to the first robot 180. The transferring the cognitive state profile to the first robot can be accomplished using various communication techniques such as by wireless communication, by tethering the robot, by reprogramming the robot, and so on. The transferring the cognitive state profile to the first toy can be accomplished using wired, wireless, or hybrid networks such as the Internet or other computer network. In embodiments, the transferring is accomplished by transferring the cognitive state profile from a second robot 182 to the first robot. As before, the transferring can be accomplished using wireless techniques, wired techniques, programming techniques, swapping out storage media, transferring data over a network, etc. The flow 100 includes providing stimuli by a first robot 190 to the individual based on the comparing. The stimuli that can be provided can include stimuli that can be detected by various human senses. In embodiments, providing stimuli can include visual stimuli, auditory stimuli, or haptic stimuli. The visual stimuli can include characters and images on a screen, lights, flashes, etc. The auditory stimuli can include voice, music, alarms, and so on. The haptic stimuli can include shakes, buzzes, vibrations, force feedback, etc. In embodiments, the providing stimuli can include providing positive reinforcement 192 for an educational effort. In other embodiments, the providing positive reinforcement can include therapeutic efforts, treatment efforts, and so on. When the robot can be a robotic humanoid, positive reinforcement can include a smile. When the robot is a robotic pet, the positive reinforcement can include purring, tail wagging, cuddling, etc. Various steps in the flow 100 may be changed in order, repeated, omitted, or the like without departing from the disclosed concepts. Various embodiments of the flow 100 can be included in a computer program product embodied in a non-transitory computer readable medium that includes code executable by one or more processors. Various embodiments of the flow 100, or portions thereof, can be included on a semiconductor chip and implemented in special purpose logic, programmable logic, and so on. Various embodiments of flow 100, or portions thereof, can be used for a processor-implemented method for robot control.

Figure 2:
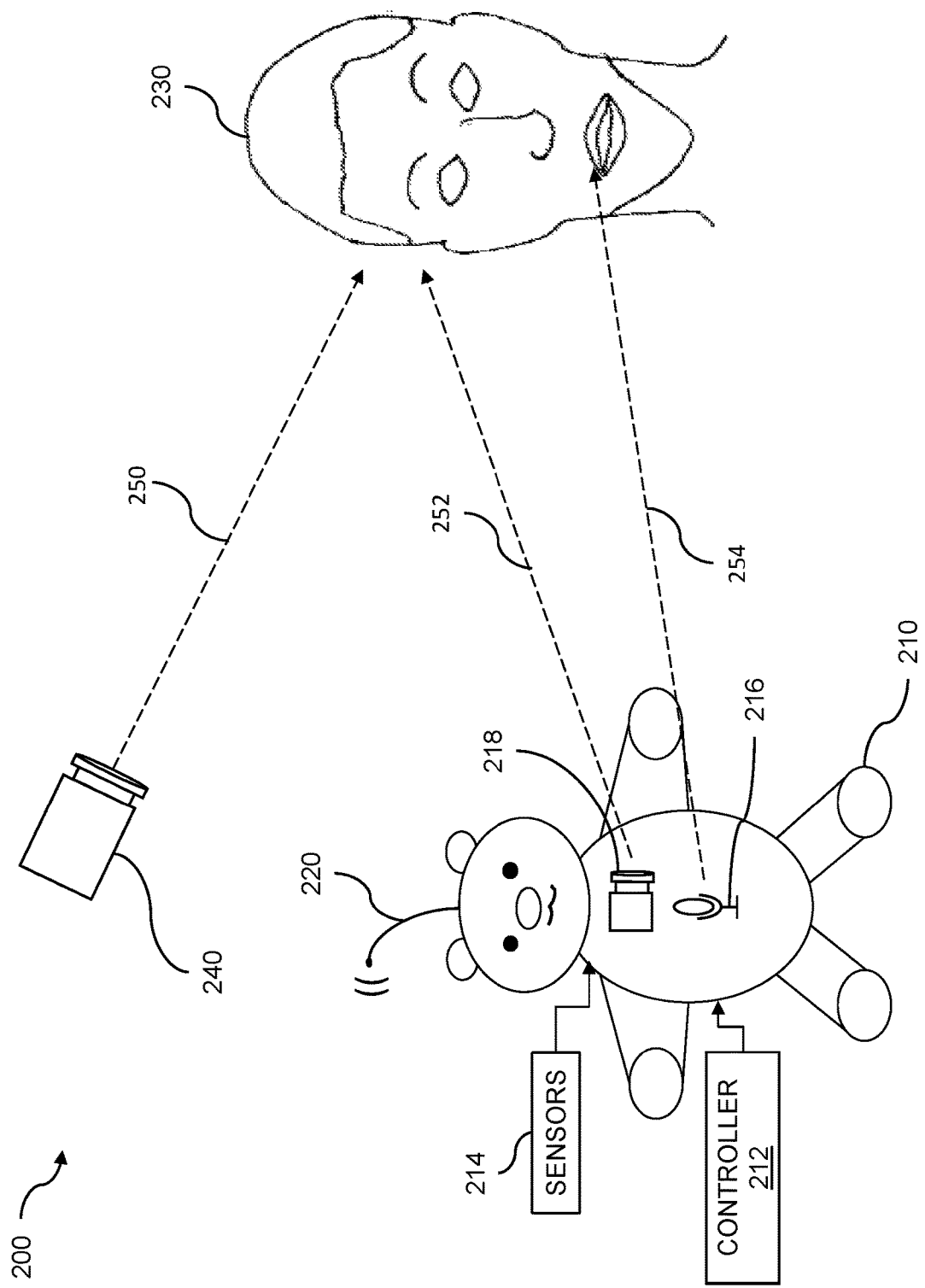
FIG. 2 illustrates a robot smart toy.

FIG. 2 illustrates a robot smart toy. An individual can interact with a robot smart toy for play, therapy, education, monitoring, and so on. The interaction with the robot smart toy can use image analysis to provide stimuli to the individual. Cognitive state data can be obtained for an individual, where the cognitive state data can include facial data and audio data for the individual. A cognitive state profile can be learned for the individual using the cognitive state data. Further cognitive state data can be collected and compared to the cognitive state profile. The stimuli can be provided by a first robot smart toy to the individual based on the comparing. Illustration 200 shows robot smart toy 210. While a teddy bear is shown, the robot smart toy can be a doll; an action figure; a car, truck, or another vehicle; a robotic humanoid; a robotic pet; a plush toy; a drone; and so on. An individual 230 can interact with the robot smart toy 210. The robot smart toy 210 can be coupled to a controller 212. The controller 212 can provide communications, rendering of data and stimuli, capturing of data, sharing of data, and so on. Sensors 214 can be coupled to the robot smart toy. The sensors can be used for collecting data relating to the individual, relating to the environment, and so on. In embodiments, the collecting of data by the first robot smart toy can include temperature of the individual, heart rate information for the individual, or accelerometer data for the first robot smart toy. In further embodiments, the collecting, by the first robot smart toy, can include physiological information for the individual.

The robot smart toy 210 can be coupled to a microphone 216, audio transducer, or other audio capture apparatus. The microphone 216 can be used for collecting voice data, audio data, etc. The voice data can be used for augmenting the cognitive state data with the voice data. The microphone 216 can detect voice data 254 from the individual 230. In embodiments, the voice data includes audio data, where the audio data can include ambient sounds, breathing sounds, vocalizations, non-speech vocalizations, and so on. The audio data can provide context for the first robot smart toy, where context can include the toy in use, not in use, used outside, used inside, etc. In embodiments, the voice data that can be captured can be used for performing voice recognition for the individual. The voice data can be evaluated to determine a cognitive state of the individual. In embodiments, the evaluating includes evaluating the voice data for timbre, prosody, vocal register, vocal resonance, pitch, loudness, speech rate, or language content. The evaluating can include determining a cognitive state, a mental state, an emotional state, a mood, and so on. In embodiments, the augmenting the cognitive state data can be based on lexical analysis of the voice data that evaluates sentiment.

The robot smart toy 210 can be coupled to a camera 218. The camera 218 can have a line of sight 252 to the individual 230. The facial data can be obtained from the camera 218 inside of the robot smart toy. More than one camera can be coupled to the robot smart toy. The camera or cameras can include a webcam, where a webcam can include a video camera, a still camera, a thermal imager, a CCD device, a phone camera, a three-dimensional camera, a depth camera, a light field (plenoptic) camera, multiple webcams used to show different views of a person, or any other type of image capture apparatus that can allow captured data to be used in an electronic system. The robot smart toy 210 can be coupled to an antenna 220. The antenna 220 can be placed inside the robot smart toy or outside the robot smart toy. The antenna 220 can be used for wirelessly transferring cognitive state data, facial data, voice data, audio data, cognitive state profiles, stimuli, and so on. The antenna can be used to connect the robot smart toy to a server, a computer, a handheld digital device, or other robot smart toys. A camera 240 can have a line of sight 250 to the individual 230. The camera 240 can be a webcam or other type of camera as described above. The camera can be used for obtaining cognitive state data, facial data, audio data, physiological data, etc., for the individual, and so on. The cognitive state data can be obtained from a camera outside of the robot smart toy, such as camera 240. The obtaining cognitive state data can be accomplished using a camera in a room occupied by the individual.

Figure 3:
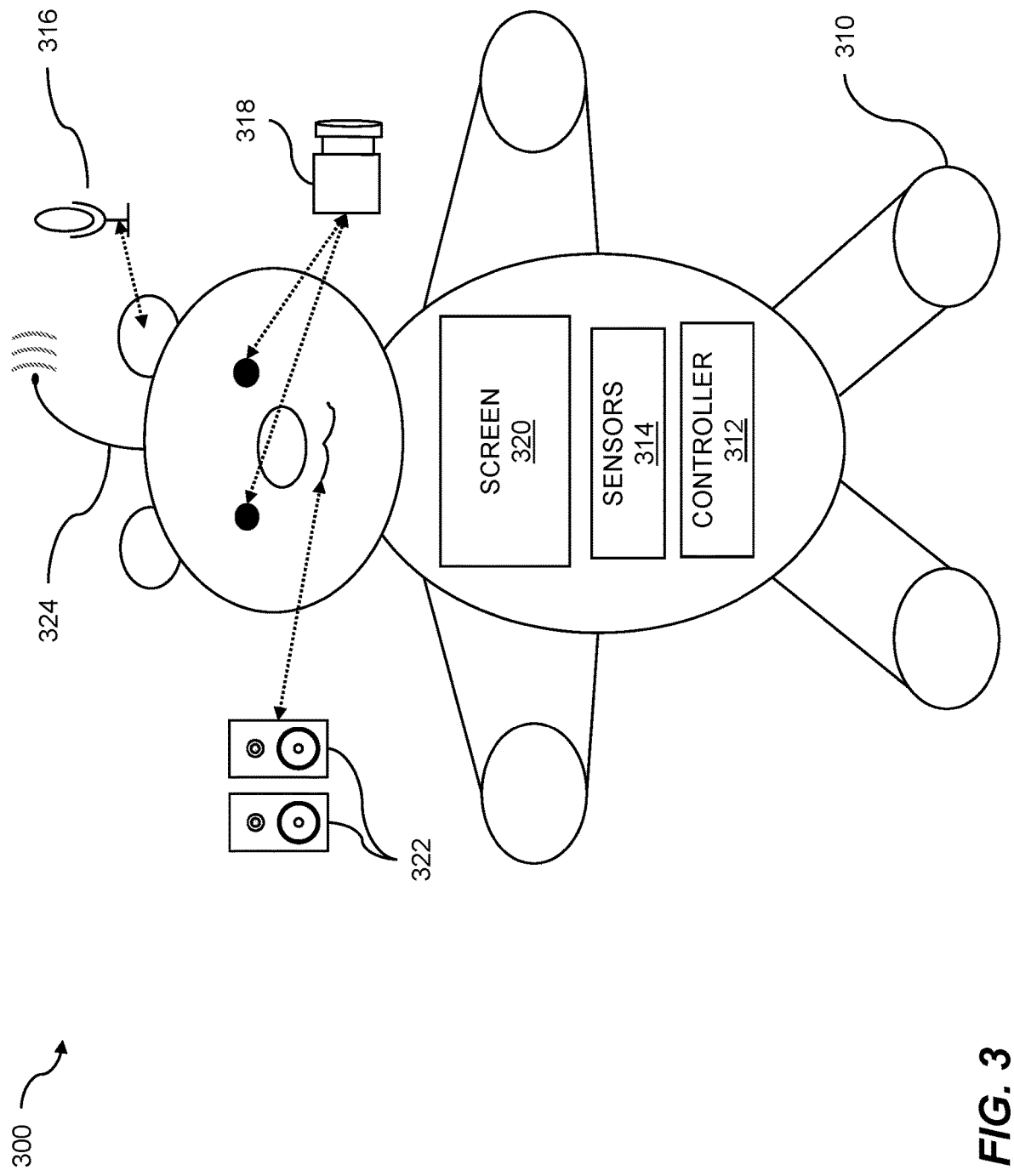
FIG. 3 shows a robot smart toy interior.

FIG. 3 shows a robot smart toy interior 300. An individual, as described elsewhere, can interact with a robot smart toy. The robot smart toy can be provided to serve a variety of purposes including education, training, companionship, therapy, monitoring, and so on. Cognitive state data, including facial data and voice data, can be obtained for an individual. A cognitive state profile can be learned for the individual using the cognitive state data, the facial data, and the voice data that was obtained. Further cognitive state data can be collected for the individual, and can be compared with the cognitive state profile. Stimuli can be provided by a first robot smart toy to the individual based on the comparing. An example smart toy 310 is shown. The smart toy can be a teddy bear; a doll; an action figure; a car, truck, or other vehicle; a robotic humanoid; a robotic pet; and so on. The smart toy can be a plush toy. The smart toy 310 can include a controller 312. The controller 312 can collect cognitive state data, including facial data and voice data for an individual, send and receive data, receive stimuli, share stimuli with other smart toys, and so on. The controller 312 can be coupled to sensors 314. The sensors 314 can be used for data collection including ambient data, data relating to the individual, and so on. In embodiments, the data that can be collected by a first smart toy can include temperature of the individual, heart rate information for the individual, or accelerometer data for the first smart toy. Other cognitive state data can be collected for the individual. In embodiments, the collecting, by the first smart toy, can include physiological information for the individual.

The smart toy 310 can be coupled to a microphone 316, an audio transducer, or other audio capture apparatus. The microphone 316 can be used for collecting voice data, speech data, etc., and augmenting the cognitive state data with the voice data. In embodiments, the voice data can include audio data. In further embodiments, the controller 312 or other technique can be used for performing voice recognition for the individual. The smart toy can be coupled to a camera 318. The camera can obtain facial data, where the facial data is obtained from a camera inside of the smart toy. The camera or cameras can include a webcam, where a webcam can include a video camera, a still camera, a thermal imager, a CCD device, a phone camera, a three-dimensional camera, a depth camera, a light field (plenoptic) camera, multiple webcams used to show different views of a person, or any other type of image capture apparatus that can allow captured data to be used in an electronic system. Further embodiments include performing facial recognition for the individual. The smart toy 310 can be coupled to a screen 320. The screen can be used for displaying visual stimuli to the individual interacting with the smart toy. The screen can be an LCD screen, an LED screen, an e-paper screen, and so on. The toy 310 can be coupled to one or more speakers 322. The speakers 322 can include audio transducers and other audio apparatus that can be used for producing audio signals for the benefit of the individual interacting with the smart toy. The smart toy 310 can include an antenna 324. The antenna 324 can be used for sending and receiving wireless signals with a server (not shown), with other smart toys (not shown), and so on.

Figure 4:
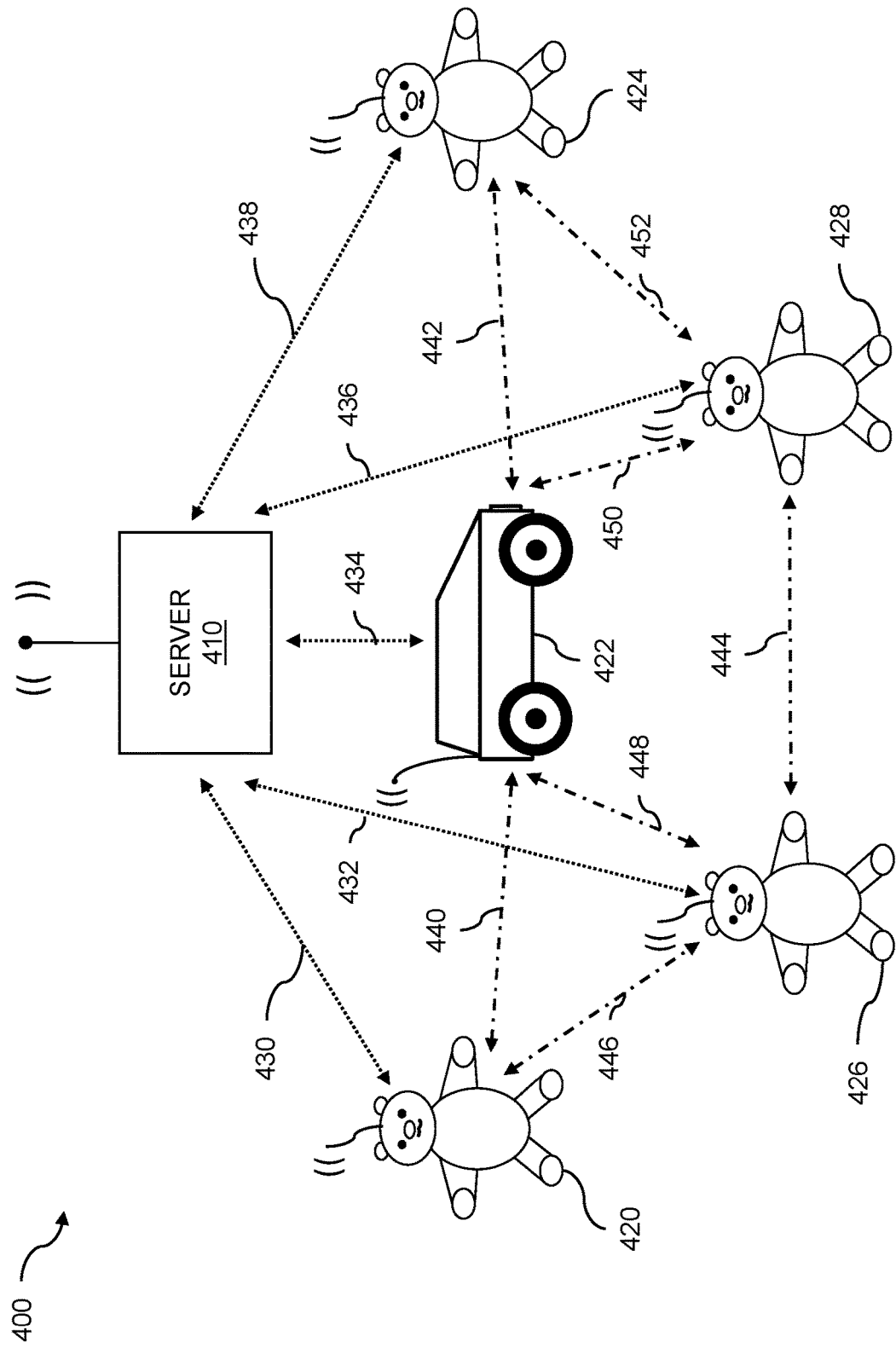
FIG. 4 illustrates an assembly of robot toys.

FIG. 4 illustrates an assembly of robot toys. Interaction with a robot toy can be based on a profile. Profiles can be used for robotic control. Cognitive state data for an individual is obtained. A cognitive state profile for the individual is learned using the cognitive state data that was obtained. Further cognitive state data for the individual is collected. The further cognitive state data is compared with the cognitive state profile. Stimuli are provided by a robot to the individual based on the comparing.

An example assembly of robot toys is shown 400. The individual can interact with an assembly of toys where the toys can include different types of toys. The toys can include teddy bears, dolls, action figures, cars and other vehicles, robotic humanoids, robotic pets, and so on. In embodiments, the facial data can be obtained from a camera outside of the smart toy. In other embodiments, the facial data can be obtained from a camera housed inside of the one or more smart toys. Voice data can also be collected using a microphone or other audio capture technique. The microphone can be located outside of the toys, housed inside one or more of the toys, etc. In embodiments, the collecting includes collecting voice data and augmenting the cognitive state data with the voice data. The collected voice data can also include audio data, which can include non-speech sounds such as laughter, grunts, squeals, singing, coughs, and so on. The interacting of the individual with the assembly of toys can include several purposes such as education, training, companionship, therapy, monitoring, and so on. In embodiments, the providing stimuli can include providing positive reinforcement for an educational effort.

The assembly of robot toys shown includes a first teddy bear smart toy 420, a car smart toy 422, a second teddy bear smart toy 424, a third teddy bear smart toy 426, and a fourth teddy bear smart toy 428. In practice, any number of toys and types of toys can be included in the assembly of toys. The collecting of facial data from a camera outside of one or more of the smart toys, the collecting the voice audio data using a microphone outside of one or more of the toys, the providing of stimuli to the smart toys, the sharing of cognitive state data among the smart toys, and so on, can be coordinated by a server 410. The server can communicate with a network such as the Internet or other computer network. The server 410 can communicate with the smart toys wirelessly. The server can communicate 430 with smart toy 420, can communicate 434 with smart toy 422, can communicate 438 with smart toy 424, can communicate 432 with smart toy 426, and can communicate 436 with smart toy 428. The server can communicate with additional smart toys (not shown) in like manner. The server can control the toys, monitor the toys, create a network for the toys, share information among the toys, transfer data to and from the toys, etc. The toys can form a network among themselves. The network can be a nearest neighbor network, an ad hoc network, a self-organizing network, a store-and-forward network, and so on. Example 400 shows wireless links among the toys including link 440 between smart toys 420 and 422, link 442 between smart toys 422 and 424, link 446 between smart toys 420 and 426, link 448 between smart toys 422 and 426, link 444 between smart toys 426 and 428, link 450 between smart toys 422 and 428, and link 452 between smart toys 424 and 428. In practice, other linking configurations can be supported.

Figure 5:
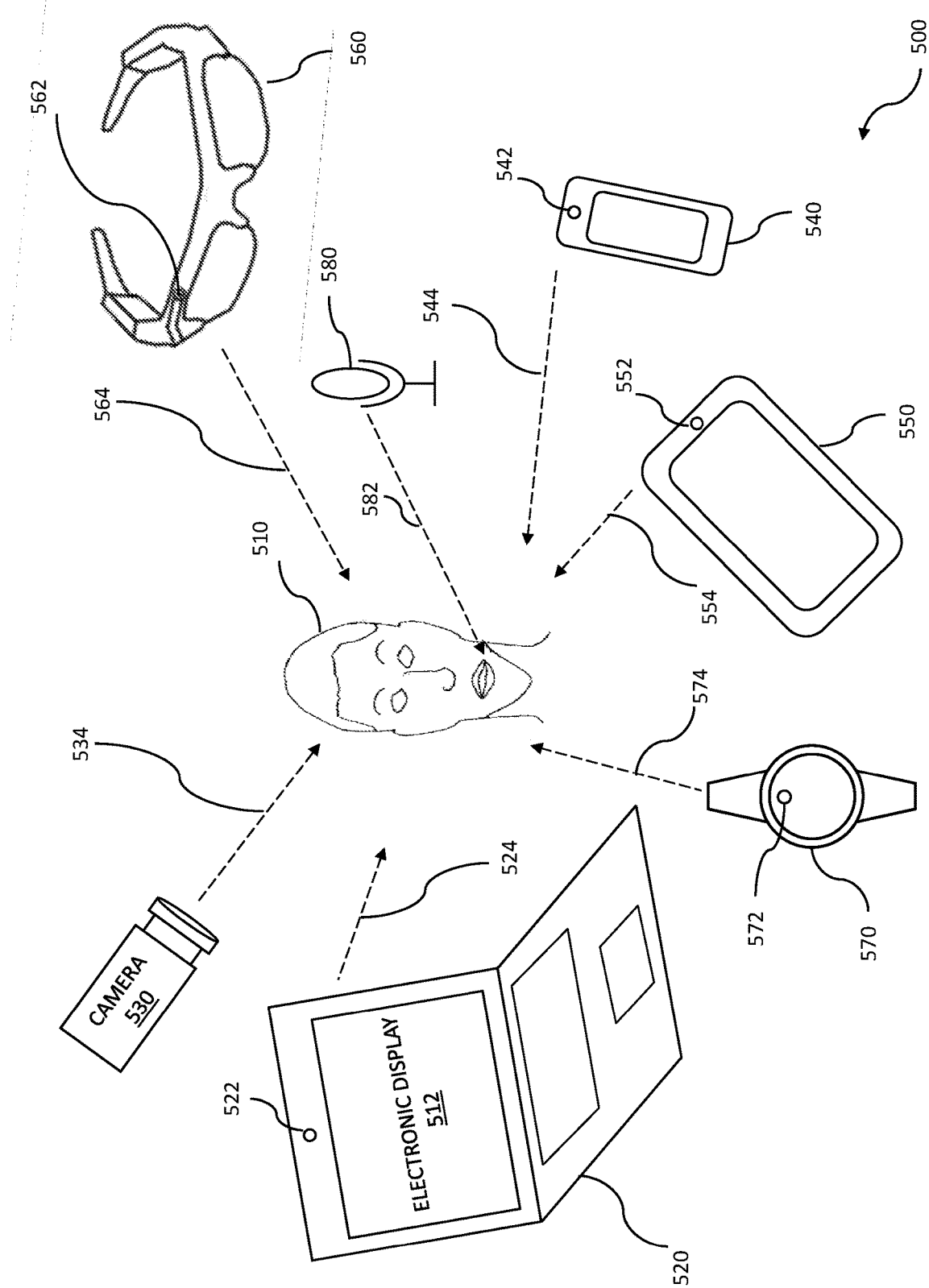
FIG. 5 shows example image and audio collection including multiple mobile devices.

FIG. 5 shows example image and audio collection including multiple mobile devices. Image and audio collection can enable interaction with a robot that is based on a profile. Profiles can be used for robotic control. Cognitive state data for an individual is obtained. A cognitive state profile for the individual is learned using the cognitive state data that was obtained. Further cognitive state data for the individual is collected. The further cognitive state data is compared with the cognitive state profile. Stimuli are provided by a robot to the individual based on the comparing. While one person is shown, in practice the video data can be collected on any number of people. In the diagram 500, the multiple mobile devices can be used separately or in combination to collect video data, audio data, or both video data and audio data on a user 510. While one person is shown, the video data and audio data can be collected on multiple people. A user 510 can be observed as she or he is performing a task, experiencing an event, viewing a media presentation, and so on. The user 510 can be shown one or more media presentations, political presentations, social media presentations, or another form of displayed media. The one or more media presentations can be shown to a plurality of people. The media presentations can be displayed on an electronic display 512 or another display. The data collected on the user 510 or on a plurality of users can be in the form of one or more videos, video frames, still images, audio channels, etc. The plurality of video data and audio data can be of people who are experiencing different situations. Some example situations can include the user or plurality of users being exposed to TV programs, movies, video clips, social media, and other such media. The situations could also include exposure to media such as advertisements, political messages, news programs, and so on.

As noted before, video data and audio data can be collected on one or more users in substantially identical or different situations and viewing either a single media presentation or a plurality of presentations. The data collected on the user 510 can be analyzed and viewed for a variety of purposes including expression analysis, cognitive state analysis, mental state analysis, emotional state analysis, and so on. The electronic display 512 can be on a laptop computer 520 as shown, a tablet computer 550, a cell phone 540, a television, a mobile monitor, or any other type of electronic device. In one embodiment, video data including expression data is collected on a mobile device such as a cell phone 540, a tablet computer 550, a laptop computer 520, or a watch 570 (or another wearable watch-type device). Similarly, the audio data including speech data and non-speech vocalizations can be collected on one or more of the mobile devices. Thus, the multiple sources can include at least one mobile device, such as a cell phone 540 or a tablet computer 550, or a wearable device such as a watch 570 or glasses 560. A mobile device can include a forward-facing camera and/or a rear-facing camera that can be used to collect expression data. A mobile device can include a microphone, audio transducer, or other audio capture apparatus that can be used to capture the speech and non-speech vocalizations. Sources of expression data can include a webcam 522, a phone camera 542, a tablet camera 552, a wearable camera 562, and a mobile camera 530. A wearable camera can comprise various camera devices, such as a watch camera 572. Sources of audio data 582 can include a microphone 580.

As the user 510 is monitored, the user 510 might move due to the nature of the task, boredom, discomfort, distractions, or for another reason. As the user moves, the camera with a view of the user's face can be changed. Thus, as an example, if the user 510 is looking in a first direction, the line of sight 524 from the webcam 522 is able to observe the user's face, but if the user is looking in a second direction, the line of sight 534 from the mobile camera 530 is able to observe the user's face. Furthermore, in other embodiments, if the user is looking in a third direction, the line of sight 544 from the phone camera 542 is able to observe the user's face, and if the user is looking in a fourth direction, the line of sight 554 from the tablet camera 552 is able to observe the user's face. If the user is looking in a fifth direction, the line of sight 564 from the wearable camera 562, which can be a device such as the glasses 560 shown and can be worn by another user or an observer, is able to observe the user's face. If the user is looking in a sixth direction, the line of sight 574 from the watch 570, with watch camera 572 included on the device, is able to observe the user's face. In other embodiments, the wearable device is another device, such as an earpiece with a camera, a helmet or hat with a camera, a clip-on camera attached to clothing, or any other type of wearable device with a camera or other sensor for collecting expression data. The user 510 can also use a wearable device including a camera for gathering contextual information and/or collecting expression data on other users. Because the user 510 can move her or his head, the facial data can be collected intermittently when she or he is looking in a direction of a camera. In some cases, multiple people can be included in the view from one or more cameras, and some embodiments include filtering out faces of one or more other people to determine whether the user 510 is looking toward a camera. All or some of the expression data can be continuously or sporadically available from the various devices and other devices.

The captured video data can include facial expressions, and can be analyzed on a computing device such as the video capture device or on another separate device. The analysis can take place on one of the mobile devices discussed above, on a local server, on a remote server, and so on. In embodiments, some of the analysis takes place on the mobile device, while other analysis takes place on a server device. The analysis of the video data can include the use of a classifier. The video data can be captured using one of the mobile devices discussed above and sent to a server or another computing device for analysis. However, the captured video data including expressions can also be analyzed on the device which performed the capturing. The analysis can be performed on a mobile device where the videos were obtained with the mobile device and wherein the mobile device includes one or more of a laptop computer, a tablet, a PDA, a smartphone, a wearable device, and so on. In another embodiment, the analyzing comprises using a classifier on a server or another computing device other than the capturing device.

Figure 6:
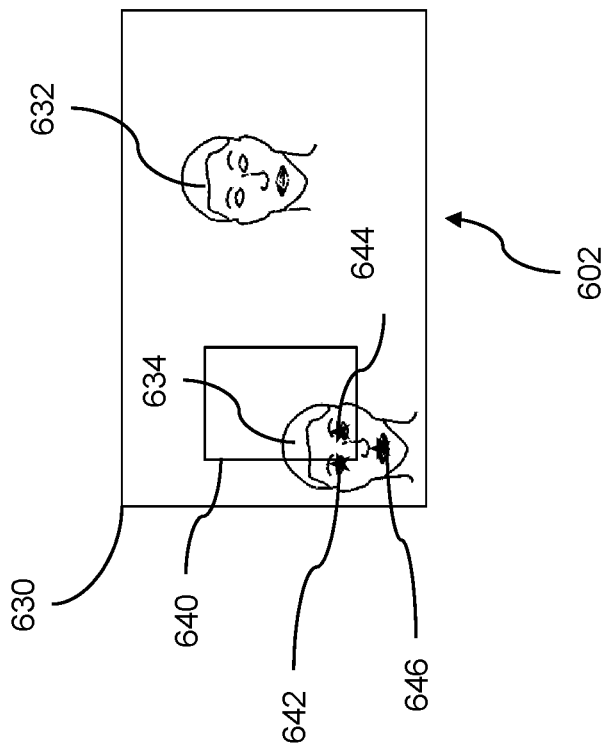
FIG. 6 illustrates feature extraction for multiple faces.
Figure 6:
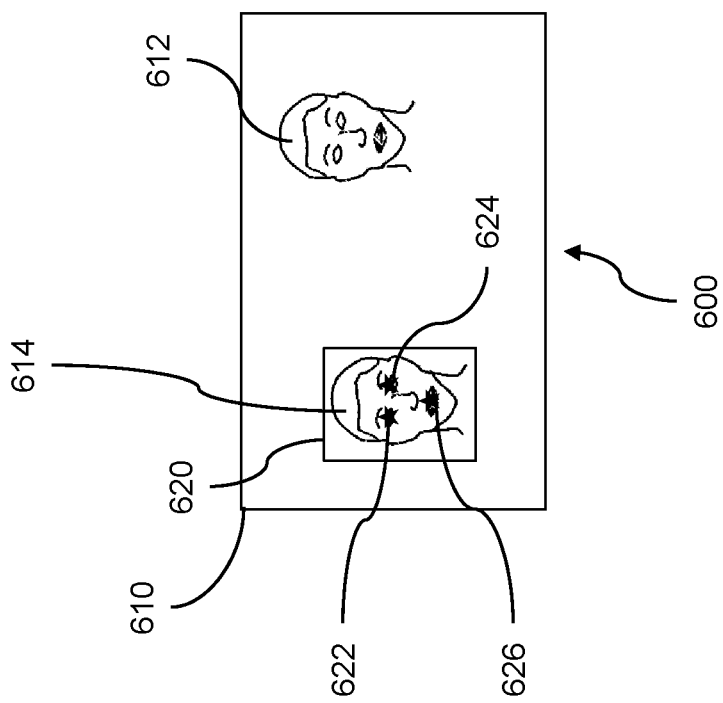

FIG. 6 illustrates feature extraction for multiple faces. Feature extraction can enable interaction with a robot that is based on a profile. Profiles can be used for robotic control. Cognitive state data for an individual is obtained. A cognitive state profile for the individual is learned using the cognitive state data that was obtained. Further cognitive state data for the individual is collected. The further cognitive state data is compared with the cognitive state profile. Stimuli are provided by a robot to the individual based on the comparing. A plurality of images can be received of an individual viewing an electronic display. A face can be identified in an image, based on the use of classifiers. The plurality of images can be evaluated to determine cognitive states and/or facial expressions of the individual. The feature extraction can be performed by analysis using one or more processors, using one or more video collection devices, and by using a server. The analysis device can be used to perform face detection for a second face, as well as for facial tracking of the first face. One or more videos can be captured, where the videos contain one or more faces. The video or videos that contain the one or more faces can be partitioned into a plurality of frames, and the frames can be analyzed for the detection of the one or more faces. The analysis of the one or more video frames can be based on one or more classifiers. A classifier can be an algorithm, heuristic, function, or piece of code that can be used to identify into which of a set of categories a new or particular observation, sample, datum, etc., should be placed. The decision to place an observation into a category can be based on training the algorithm or piece of code by analyzing a known set of data, known as a training set. The training set can include data for which category memberships of the data can be known. The training set can be used as part of a supervised training technique. If a training set is not available, then a clustering technique can be used to assign observations into categories. The latter approach, or unsupervised learning, can be based on a measure (i.e. distance) of one or more inherent similarities among the data that is being categorized. When the new observation is received, then the classifier can be used to categorize the new observation. Classifiers can be used for many analysis applications, including analysis of one or more faces. The use of classifiers can be the basis of analyzing the one or more faces for gender, ethnicity, and age; for detection of one or more faces in one or more videos; for detection of facial features; for detection of facial landmarks, and so on. The observations can be analyzed based on one or more of a set of quantifiable properties. The properties can be described as features and explanatory variables and can include various data types that can include numerical (integer-valued, real-valued), ordinal, categorical, and so on. Some classifiers can be based on a comparison between an observation and prior observations, as well as based on functions such as a similarity function, a distance function, and so on.

Classification can be based on various types of algorithms, heuristics, codes, procedures, statistics, and so on. Many techniques exist for performing classification. This classification of one or more observations into one or more groups can be based on distributions of the data values, probabilities, and so on. Classifiers can be binary, multiclass, linear, and so on. Algorithms for classification can be implemented using a variety of techniques, including neural networks, kernel estimation, support vector machines, use of quadratic surfaces, and so on. Classification can be used in many application areas such as computer vision, speech and handwriting recognition, and so on. Classification can be used for biometric identification of one or more people in one or more frames of one or more videos.

Returning to FIG. 6, the detection of the first face, the second face, and multiple faces can include identifying facial landmarks, generating a bounding box, and predicting a bounding box and landmarks for a next frame, where the next frame can be one of a plurality of frames of a video containing faces. A first video frame 600 includes a frame boundary 610, a first face 612, and a second face 614. The first video frame 600 also includes a bounding box 620. Facial landmarks can be generated for the first face 612. Face detection can be performed to initialize a second set of locations for a second set of facial landmarks for a second face within the video. Facial landmarks in the first video frame 600 can include the facial landmarks 622, 624, and 626. The facial landmarks can include corners of a mouth, corners of eyes, eyebrow corners, the tip of the nose, nostrils, chin, the tips of ears, and so on. The performing of face detection on the second face can include performing facial landmark detection with the first frame from the video for the second face and can include estimating a second rough bounding box for the second face based on the facial landmark detection. The estimating of a second rough bounding box can include the bounding box 620. Bounding boxes can also be estimated for one or more other faces within the frame boundary 610. The bounding box can be refined, as can one or more facial landmarks. The refining of the second set of locations for the second set of facial landmarks can be based on localized information around the second set of facial landmarks. The bounding box 620 and the facial landmarks 622, 624, and 626 can be used to estimate future locations for the second set of locations for the second set of facial landmarks in a future video frame from the first video frame.

A second video frame 602 is also shown. The second video frame 602 includes a frame boundary 630, a first face 632, and a second face 634. The second video frame 602 also includes a bounding box 640 and the facial landmarks 642, 644, and 646. In other embodiments, multiple facial landmarks are generated and used for facial tracking of the two or more faces of a video frame, such as the shown second video frame 602. Facial points from the first face can be distinguished from other facial points. In embodiments, the other facial points include facial points of one or more other faces. The facial points can correspond to the facial points of the second face. The distinguishing of the facial points of the first face and the facial points of the second face can be used to distinguish between the first face and the second face, to track either or both of the first face and the second face, and so on. Other facial points can correspond to the second face. As mentioned above, multiple facial points can be determined within a frame. One or more of the other facial points that are determined can correspond to a third face. The location of the bounding box 640 can be estimated, where the estimating can be based on the location of the generated bounding box 620 shown in the first video frame 600. The three facial landmarks shown, facial landmarks 642, 644, and 646, might lie within the bounding box 640 or might not lie partially or completely within the bounding box 640. For instance, the second face 634 might have moved between the first video frame 600 and the second video frame 602. Based on the accuracy of the estimating of the bounding box 640, a new estimation can be determined for a third, future frame from the video, and so on. The evaluation can be performed, all or in part, on semiconductor-based logic. The evaluation can be used to infer an emotion metric.

Figure 7:
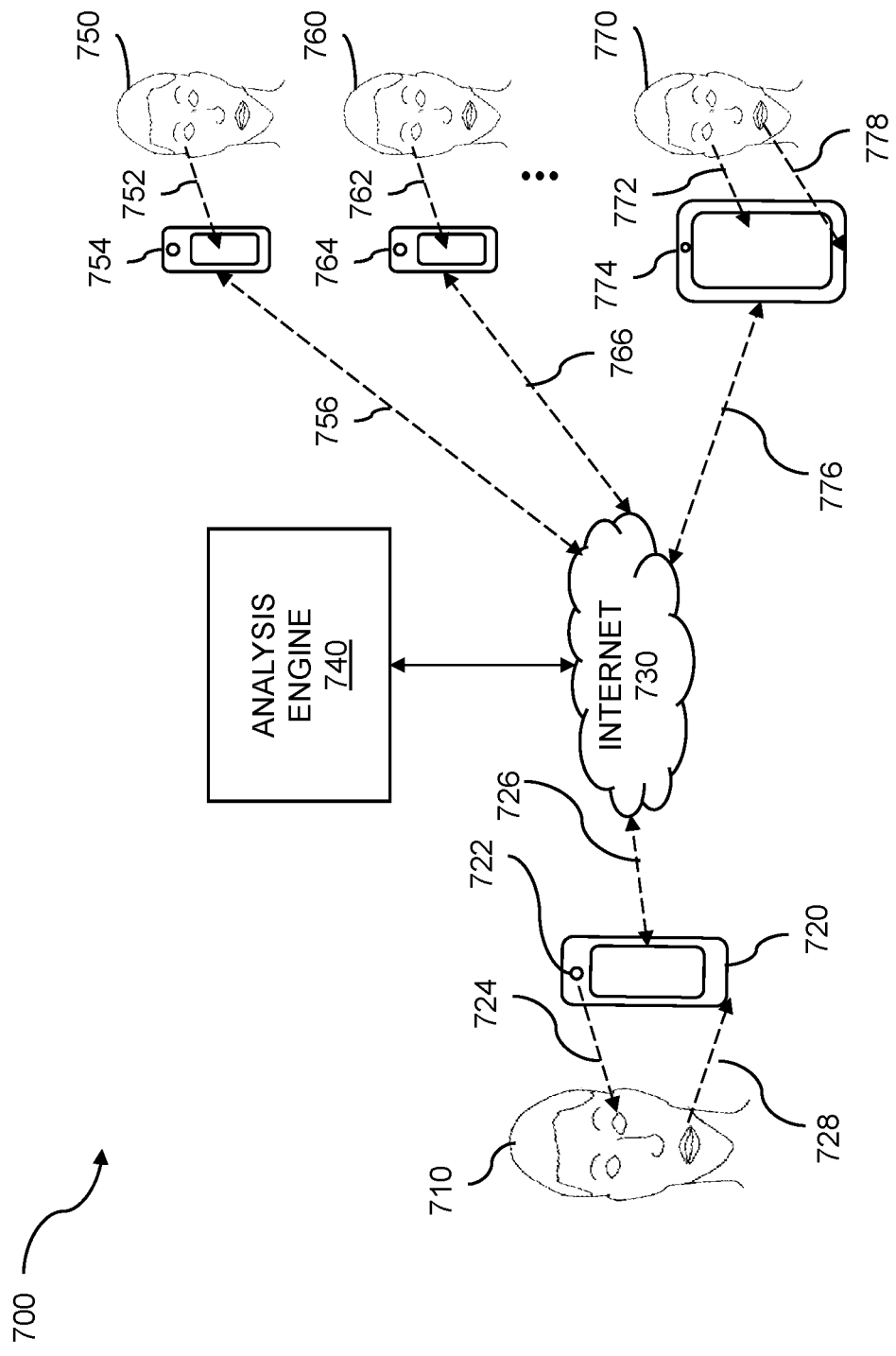
FIG. 7 shows an example of livestreaming of social video and audio.

FIG. 7 shows an example of livestreaming of social video and audio. The streaming of social video and social audio can be applied to robotic control using profiles. The livestreaming can include cognitive state data, facial data, audio data, etc., that can be obtained and used for learning a cognitive state profile for an individual. Further cognitive state data can be collected from the individual and compared with the cognitive state profile. Stimuli can be provided by a first robot to the individual based on the comparing. The streaming and analysis can be facilitated by a video capture device, a local server, a remote server, a semiconductor-based logic, and so on. The streaming can be livestreaming and can include cognitive state analysis, cognitive state event signature analysis, etc. Livestreaming video is an example of one-to-many social media, where video can be sent over the Internet from one person to a plurality of people using a social media app and/or platform. Livestreaming is one of numerous popular techniques used by people who want to disseminate ideas, send information, provide entertainment, share experiences, and so on. Some of the livestreams can be scheduled, such as webcasts, online classes, sporting events, news, computer gaming, or video conferences, while others can be impromptu streams that are broadcast as needed or when desirable. Examples of impromptu livestream videos can range from individuals simply wanting to share experiences with their social media followers, to live coverage of breaking news, emergencies, or natural disasters. The latter coverage is known as mobile journalism, or "mo jo", and is becoming increasingly common. With this type of coverage, news reporters can use networked, portable electronic devices to provide mobile journalism content to a plurality of social media followers. Such reporters can be quickly and inexpensively deployed as the need or desire arises.

Several livestreaming social media apps and platforms can be used for transmitting video. One such video social media app is Meerkat™ which can link with a user's Twitter™ account. Meerkat™ enables a user to stream video using a handheld, networked electronic device coupled to video capabilities. Viewers of the livestream can comment on the stream using tweets that can be seen by and responded to by the broadcaster. Another popular app is Periscope™ which can transmit a live recording from one user to his or her Periscope™ account and to other followers. The Periscope™ app can be executed on a mobile device. The user's Periscope™ followers can receive an alert whenever that user begins a video transmission. Another livestream video platform is Twitch™ which can be used for video streaming of video gaming and broadcasts of various competitions and events.

The example 700 shows a user 710 broadcasting a video livestream and an audio livestream to one or more people as shown by a first person 750, a second person 760, and a third person 770. A network-enabled, portable electronic device 720 can be coupled to a front-facing camera 722. The portable electronic device 720 can be a smartphone, a PDA, a tablet, a laptop computer, and so on. The front-facing camera 722 coupled to the portable electronic device 720 can have a line-of-sight view 724 to the user 710 and can capture video of the user 710. The portable electronic device 720 can be coupled to a microphone (not shown). The microphone can capture voice data 728 such as speech and non-speech vocalizations. In embodiments, non-speech vocalizations can include grunts, yelps, squeals, snoring, sighs, laughter, filled pauses, unfilled pauses, yawns, and the like. The captured video and audio can be sent to an analysis or recommendation engine 740 using a network link 726 to the Internet 730. The network link can be a wireless link, a wired link, and so on. The recommendation engine 740 can recommend to the user 710 an app and/or platform that can be supported by the server and can be used to provide a video livestream, an audio livestream, or both a video livestream and an audio livestream to one or more followers of the user 710.

In the example 700, the user 710 has three followers: a first person 750, a second person 760, and a third person 770. Each follower has a line-of-sight view to a video screen on a portable, networked electronic device. In other embodiments, one or more followers follow the user 710 using any other networked electronic device, including a computer. In the example 700, a first person 750 has a line-of-sight view 752 to the video screen of a device 754; a second person 760 has a line-of-sight view 762 to the video screen of a device 764, and a third person 770 has a line-of-sight view 772 to the video screen of a device 774. The device 774 can also capture audio data 778 from the third person 770. The devices 754, 764, and 774, which can be portable electronic devices, can each be a smartphone, a PDA, a tablet, and so on. Each portable device can receive the video stream and the audio stream being broadcast by the user 710 through the Internet 730 using the app and/or platform that can be recommended by the recommendation engine 740. The device 754 can receive a video stream and the audio stream using the network link 756, the device 764 can receive a video stream and the audio stream using the network link 766, the device 774 can receive a video stream and the audio stream using the network link 776, and so on. The network link can be a wireless link, a wired link, a hybrid link, and so on. Depending on the app and/or platform that can be recommended by the recommendation engine 740, one or more followers, such as the followers shown (first person 750, second person 760, and third person 770), can reply to, comment on, or otherwise provide feedback to the user 710 using their respective devices 754, 764, and 774.

The human face provides a powerful communications medium through its ability to exhibit numerous expressions that can be captured and analyzed for a variety of purposes. In some cases, media producers have a keen interest in evaluating the effectiveness of message delivery by video media. Such video media includes advertisements, political messages, educational materials, television programs, movies, government service announcements, etc. Automated facial analysis can be performed on one or more video frames containing a face in order to detect facial action. Based on the facial action detected, a variety of parameters can be determined, including affect valence, spontaneous reactions, facial action units, and so on. The parameters that are determined can be used to infer or predict emotional, mental, and cognitive states. For example, determined valence can be used to describe the emotional reaction of a viewer to a video media presentation or another type of presentation. Positive valence provides evidence that a viewer is experiencing a favorable emotional response to the video media presentation, while negative valence provides evidence that a viewer is experiencing an unfavorable emotional response to the video media presentation. Other facial data analysis can include the determination of discrete emotional states of the viewer or viewers.

Facial data can be collected from a plurality of people using any of a variety of cameras. A camera can include a webcam, a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. In some embodiments, the person is permitted to "opt-in" to the facial data collection. For example, the person can agree to the capture of facial data using a personal device such as a mobile device or another electronic device by selecting an opt-in choice. Opting-in can then turn on the person's webcam-enabled device and can begin the capture of the person's facial data via a video feed from the webcam or other camera. The video data that is collected can include one or more persons experiencing an event. The one or more persons can be sharing a personal electronic device or can each be using one or more devices for video capture. The videos that are collected can be collected using a web-based framework. The web-based framework can be used to display the video media presentation or event as well as to collect videos from multiple viewers who are online. That is, the collection of videos can be crowdsourced from those viewers who elected to opt in to the video data collection.

The videos captured from the various viewers who chose to opt in can be substantially different in terms of video quality, frame rate, etc. As a result, the facial video data can be scaled, rotated, and otherwise adjusted to improve consistency. Human factors further contribute to the capture of the facial video data. The facial data that is captured might or might not be relevant to the video media presentation being displayed. For example, the viewer might not be paying attention, might be fidgeting, might be distracted by an object or event near the viewer, or might be otherwise inattentive to the video media presentation. The behavior exhibited by the viewer can prove challenging to analyze due to viewer actions including eating, speaking to another person or persons, speaking on the phone, etc. The videos collected from the viewers might also include other artifacts that pose challenges during the analysis of the video data. The artifacts can include items such as eyeglasses (because of reflections), eye patches, jewelry, and clothing that occludes or obscures the viewer's face. Similarly, a viewer's hair or hair covering can present artifacts by obscuring the viewer's eyes and/or face.

The captured facial data can be analyzed using the facial action coding system (FACS). The FACS seeks to define groups or taxonomies of facial movements of the human face. The FACS encodes movements of individual muscles of the face, where the muscle movements often include slight, instantaneous changes in facial appearance. The FACS encoding is commonly performed by trained observers, but can also be performed on automated, computer-based systems. Analysis of the FACS encoding can be used to determine emotions of the persons whose facial data is captured in the videos. The FACS is used to encode a wide range of facial expressions that are anatomically possible for the human face. The FACS encodings include action units (AUs) and related temporal segments that are based on the captured facial expression. The AUs are open to higher order interpretation and decision-making. These AUs can be used to recognize emotions experienced by the person who is being observed. Emotion-related facial actions can be identified using the emotional facial action coding system (EMFACS) and the facial action coding system affect interpretation dictionary (FACSAID). For a given emotion, specific action units can be related to the emotion. For example, the emotion of anger can be related to AUs 4, 5, 7, and 23, while happiness can be related to AUs 6 and 12. Other mappings of emotions to AUs have also been previously associated. The coding of the AUs can include an intensity scoring that ranges from A (trace) to E (maximum). The AUs can be used for analyzing images to identify patterns indicative of a particular cognitive and/or emotional state. The AUs range in number from 0 (neutral face) to 98 (fast up-down look). The AUs include so-called main codes (inner brow raiser, lid tightener, etc.), head movement codes (head turn left, head up, etc.), eye movement codes (eyes turned left, eyes up, etc.), visibility codes (eyes not visible, entire face not visible, etc.), and gross behavior codes (sniff, swallow, etc.). Emotion scoring can be included where intensity is evaluated, and specific emotions, moods, mental states, or cognitive states can be identified.

The coding of faces identified in videos captured of people observing an event can be automated. The automated systems can detect facial AUs or discrete emotional states. The emotional states can include amusement, fear, anger, disgust, surprise, and sadness. The automated systems can be based on a probability estimate from one or more classifiers, where the probabilities can correlate with an intensity of an AU or an expression. The classifiers can be used to identify into which of a set of categories a given observation can be placed. In some cases, the classifiers can be used to determine a probability that a given AU or expression is present in a given frame of a video. The classifiers can be used as part of a supervised machine learning technique, where the machine learning technique can be trained using "known good" data. Once trained, the machine learning technique can proceed to classify new data that is captured.

The supervised machine learning models can be based on support vector machines (SVMs). An SVM can have an associated learning model that is used for data analysis and pattern analysis. For example, an SVM can be used to classify data that can be obtained from collected videos of people experiencing a media presentation. An SVM can be trained using "known good" data that is labeled as belonging to one of two categories (e.g. smile and no-smile). The SVM can build a model that assigns new data into one of the two categories. The SVM can construct one or more hyperplanes that can be used for classification. The hyperplane that has the largest distance from the nearest training point can be determined to have the best separation. The largest separation can improve the classification technique by increasing the probability that a given data point can be properly classified.

In another example, a histogram of oriented gradients (HoG) can be computed. The HoG can include feature descriptors and can be computed for one or more facial regions of interest. The regions of interest of the face can be located using facial landmark points, where the facial landmark points can include outer edges of nostrils, outer edges of the mouth, outer edges of eyes, etc. A HoG for a given region of interest can count occurrences of gradient orientation within a given section of a frame from a video, for example. The gradients can be intensity gradients and can be used to describe an appearance and a shape of a local object. The HoG descriptors can be determined by dividing an image into small, connected regions, also called cells. A histogram of gradient directions or edge orientations can be computed for pixels in the cell. Histograms can be contrast-normalized based on intensity across a portion of the image or the entire image, thus reducing any influence from differences in illumination or shadowing changes between and among video frames. The HoG can be computed on the image or on an adjusted version of the image, where the adjustment of the image can include scaling, rotation, etc. The image can be adjusted by flipping the image around a vertical line through the middle of a face in the image. The symmetry plane of the image can be determined from the tracker points and landmarks of the image.

In embodiments, an automated facial analysis system identifies five facial actions or action combinations in order to detect spontaneous facial expressions for media research purposes. Based on the facial expressions that are detected, a determination can be made with regard to the effectiveness of a given video media presentation, for example. The system can detect the presence of the AUs or the combination of AUs in videos collected from a plurality of people. The facial analysis technique can be trained using a web-based framework to crowdsource videos of people as they watch online video content. The video can be streamed at a fixed frame rate to a server. Human labelers can code for the presence or absence of facial actions including a symmetric smile, unilateral smile, asymmetric smile, and so on. The trained system can then be used to automatically code the facial data collected from a plurality of viewers experiencing video presentations (e.g. television programs).

Spontaneous asymmetric smiles can be detected in order to understand viewer experiences. Related literature indicates that as many asymmetric smiles occur on the right hemi face as do on the left hemi face, for spontaneous expressions. Detection can be treated as a binary classification problem, where images that contain a right asymmetric expression are used as positive (target class) samples and all other images as negative (non-target class) samples. Classifiers perform the classification, including classifiers such as support vector machines (SVM) and random forests. Random forests can include ensemble-learning methods that use multiple learning algorithms to obtain better predictive performance. Frame-by-frame detection can be performed to recognize the presence of an asymmetric expression in each frame of a video. Facial points can be detected, including the top of the mouth and the two outer eye corners. The face can be extracted, cropped, and warped into a pixel image of specific dimension (e.g. 96×96 pixels). In embodiments, the inter-ocular distance and vertical scale in the pixel image are fixed. Feature extraction can be performed using computer vision software such as OpenCV™. Feature extraction can be based on the use of HoGs. HoGs can include feature descriptors and can be used to count occurrences of gradient orientation in localized portions or regions of the image. Other techniques can be used for counting occurrences of gradient orientation, including edge orientation histograms, scale-invariant feature transformation descriptors, etc. The AU recognition tasks can also be performed using Local Binary Patterns (LBPs) and Local Gabor Binary Patterns (LGBPs). The HoG descriptor represents the face as a distribution of intensity gradients and edge directions and is robust in its ability to translate and scale. Differing patterns, including groupings of cells of various sizes and arranged in variously sized cell blocks, can be used. For example, 4×4 cell blocks of 8×8-pixel cells with an overlap of half of the block can be used. Histograms of channels can be used, including nine channels or bins evenly spread over 0-180 degrees. In this example, the HoG descriptor on a 96×96 image is 25 blocks×16 cells×9 bins=3600, the latter quantity representing the dimension. AU occurrences can be rendered. The videos can be grouped into demographic datasets based on nationality and/or other demographic parameters for further detailed analysis. This grouping and other analyses can be facilitated via semiconductor-based logic.

Figure 8:
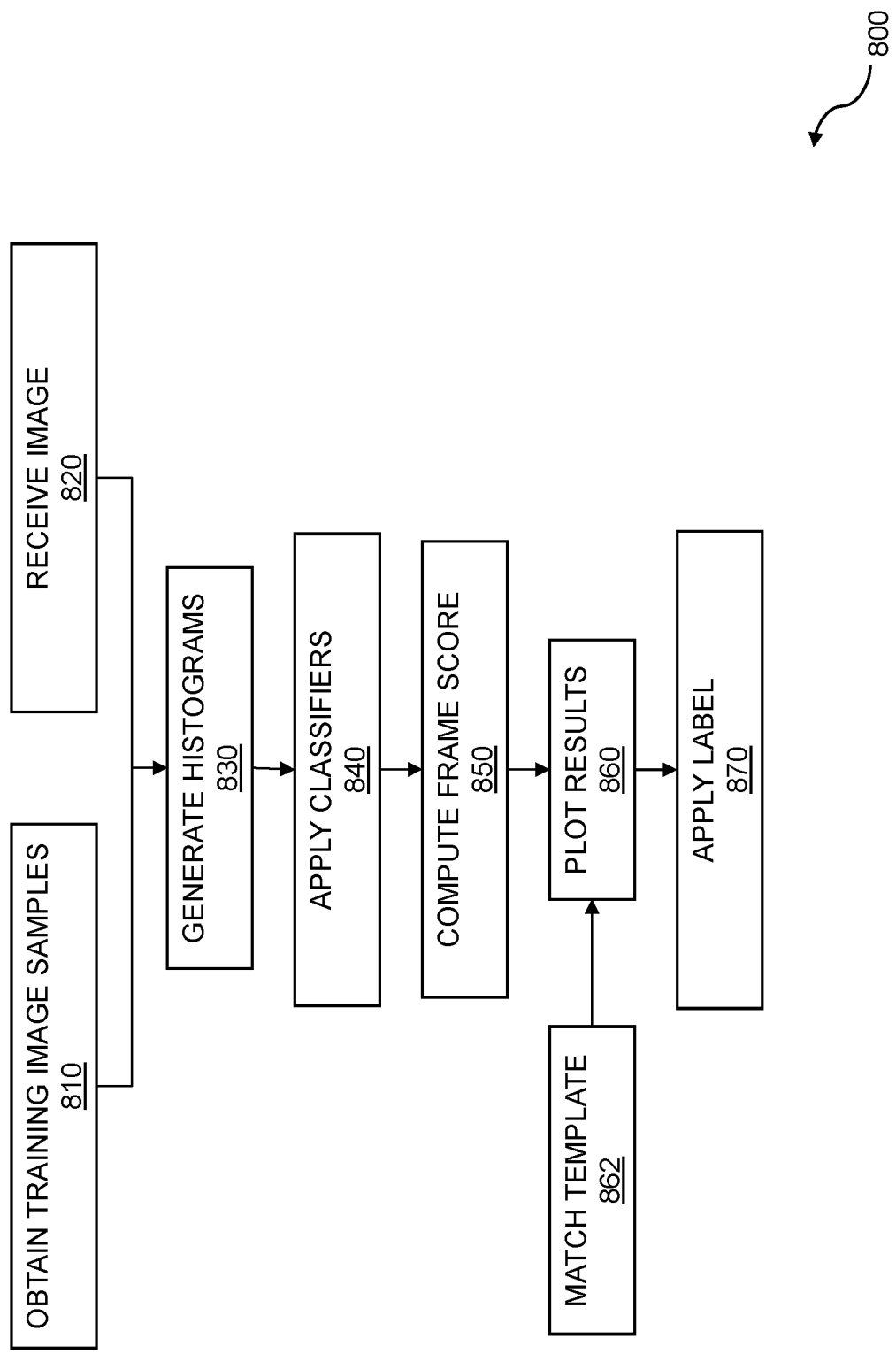
FIG. 8 is a flow diagram for detecting facial expressions.

FIG. 8 is a flow diagram for detecting facial expressions. The detection of facial expressions can be performed for robotic control using profiles. Cognitive state data for an individual is obtained. A cognitive state profile for the individual is learned using the cognitive state data that was obtained. Further cognitive state data for the individual is collected. The further cognitive state data is compared with the cognitive state profile. Stimuli are provided by a robot to the individual based on the comparing. A plurality of images can be received of an individual viewing an electronic display. A face can be identified in an image, based on the use of classifiers. The plurality of images can be evaluated to determine the cognitive states and/or facial expressions the individual. The flow 800, or portions thereof, can be implemented in semiconductor logic, can be accomplished using a mobile device, can be accomplished using a server device, and so on. The flow 800 can be used to automatically detect a wide range of facial expressions. A facial expression can produce strong emotional signals that can indicate valence and discrete emotional states. The discrete emotional states can include contempt, doubt, defiance, happiness, fear, anxiety, and so on. The detection of facial expressions can be based on the location of facial landmarks. The detection of facial expressions can be based on determination of action units (AUs), where the action units are determined using FACS coding. The AUs can be used singly or in combination to identify facial expressions. Based on the facial landmarks, one or more AUs can be identified by number and intensity. For example, AU12 can be used to code a lip corner puller and can be used to infer a smirk.

The flow 800 begins by obtaining training image samples 810. The image samples can include a plurality of images of one or more people. Human coders who are trained to correctly identify AU codes based on the FACS can code the images. The training, or "known good", images can be used as a basis for training a machine learning technique. Once trained, the machine learning technique can be used to identify AUs in other images that can be collected using a camera, a sensor, and so on. The flow 800 continues with receiving an image 820. The image 820 can be received from a camera, a sensor, and so on. As previously discussed, the camera or cameras can include a webcam, where a webcam can include a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. The image that is received can be manipulated in order to improve the processing of the image. For example, the image can be cropped, scaled, stretched, rotated, flipped, etc., in order to obtain a resulting image that can be analyzed more efficiently. Multiple versions of the same image can be analyzed. In some cases, the manipulated image and a flipped or mirrored version of the manipulated image can be analyzed alone and/or in combination to improve analysis. The flow 800 continues with generating histograms 830 for the training images and the one or more versions of the received image. The histograms can be based on a HoG or another histogram. As described in previous paragraphs, the HoG can include feature descriptors and can be computed for one or more regions of interest in the training images and the one or more received images. The regions of interest in the images can be located using facial landmark points, where the facial landmark points can include outer edges of nostrils, outer edges of the mouth, outer edges of eyes, etc. A HoG for a given region of interest can count occurrences of gradient orientation within a given section of a frame from a video.

The flow 800 continues with applying classifiers 840 to the histograms. The classifiers can be used to estimate probabilities, where the probabilities can correlate with an intensity of an AU or an expression. In some embodiments, the choice of classifiers used is based on the training of a supervised learning technique to identify facial expressions. The classifiers can be used to identify into which of a set of categories a given observation can be placed. The classifiers can be used to determine a probability that a given AU or expression is present in a given image or frame of a video. In various embodiments, the one or more AUs that are present include AU01 inner brow raiser, AU12 lip corner puller, AU38 nostril dilator, and so on. In practice, the presence or absence of multiple AUs can be determined. The flow 800 continues with computing a frame score 850. The score computed for an image, where the image can be a frame from a video, can be used to determine the presence of a facial expression in the image or video frame. The score can be based on one or more versions of the image 820 or a manipulated image. The score can be based on a comparison of the manipulated image to a flipped or mirrored version of the manipulated image. The score can be used to predict a likelihood that one or more facial expressions are present in the image. The likelihood can be based on computing a difference between the outputs of a classifier used on the manipulated image and on the flipped or mirrored image, for example. The classifier can be used to identify symmetrical facial expressions (e.g. smile), asymmetrical facial expressions (e.g. outer brow raiser), and so on.

The flow 800 continues with plotting results 860. The results that are plotted can include one or more scores for one or more frames computed over a given time t. For example, the plotted results can include classifier probability results from analysis of HoGs for a sequence of images and video frames. The plotted results can be matched with a template 862. The template can be temporal and can be represented by a centered box function or another function. A best fit with one or more templates can be found by computing a minimum error. Other best-fit techniques can include polynomial curve fitting, geometric curve fitting, and so on. The flow 800 continues with applying a label 870. The label can be used to indicate that a particular facial expression has been detected in the one or more images or video frames which constitute the image 820 that was received. The label can be used to indicate that any of a range of facial expressions has been detected, including a smile, an asymmetric smile, a frown, and so on. Various steps in the flow 800 may be changed in order, repeated, omitted, or the like without departing from the disclosed concepts. Various embodiments of the flow 800 can be included in a computer program product embodied in a non-transitory computer readable medium that includes code executable by one or more processors. Various embodiments of the flow 800, or portions thereof, can be included on a semiconductor chip and implemented in special purpose logic, programmable logic, and so on. Various embodiments of flow 800, or portions thereof, can be used for a processor-implemented method for robotic control using profiles.

Figure 9:
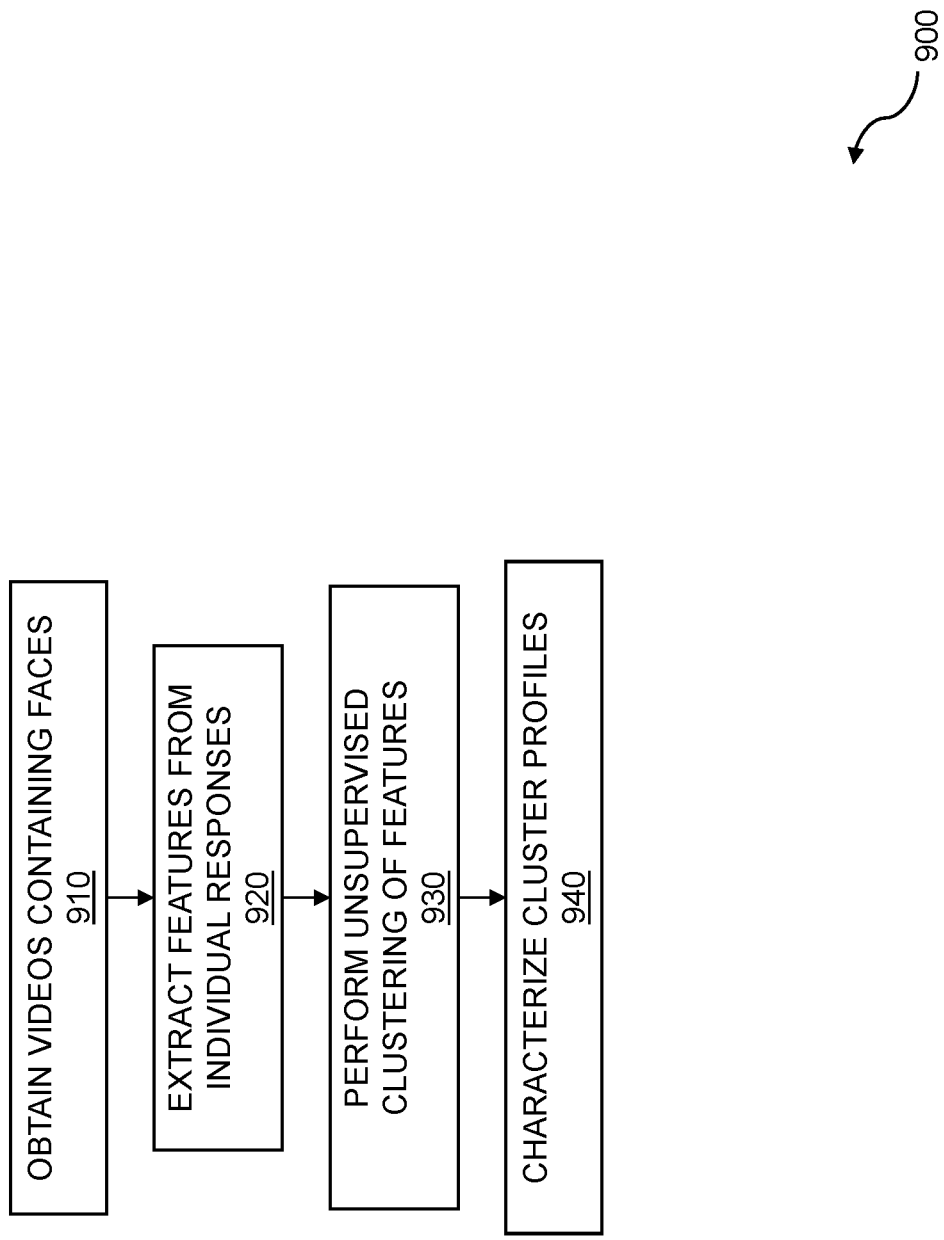
FIG. 9 is a flow diagram for the large-scale clustering of facial events.

FIG. 9 is a flow diagram for the large-scale clustering of facial events. The large-scale clustering of facial events can enable robotic control using profiles. Cognitive state data for an individual is obtained. A cognitive state profile for the individual is learned using the cognitive state data that was obtained. Further cognitive state data for the individual is collected. The further cognitive state data is compared with the cognitive state profile. Stimuli are provided by a robot to the individual based on the comparing. A plurality of images of an individual viewing an electronic display can be received. A face can be identified in an image, based on the use of classifiers. The plurality of images can be evaluated to determine the cognitive states and/or facial expressions of the individual. The clustering and evaluation of facial events can be augmented using a mobile device, a server, semiconductor-based logic, and so on. As discussed above, collection of facial video data from one or more people can include a web-based framework. The web-based framework can be used to collect facial video data from large numbers of people located over a wide geographic area. The web-based framework can include an opt-in feature that allows people to agree to facial data collection. The web-based framework can be used to render and display data to one or more people and can collect data from the one or more people. For example, the facial data collection can be based on showing a video media presentation to one or more viewers through a website. The web-based framework can be used to display the video media presentation or event and to collect videos from multiple viewers who are online. That is, the collection of videos can be crowdsourced from those viewers who elected to opt-in to the video data collection. The video event can be a commercial, a political ad, an educational segment, and so on.

The flow 900 begins with obtaining videos containing faces 910. The videos can be obtained using one or more cameras, where the cameras can include a webcam coupled to one or more devices employed by the one or more people using the web-based framework. The flow 900 continues with extracting features from the individual responses 920. The individual responses can include videos containing faces observed by the one or more webcams. The features that are extracted can include facial features such as an eyebrow, a nostril, an eye edge, a mouth edge, and so on. The feature extraction can be based on facial coding classifiers, where the facial coding classifiers output a probability that a specified facial action has been detected in a given video frame. The flow 900 continues with performing unsupervised clustering of features 930. The unsupervised clustering can be based on an event. The unsupervised clustering can be based on a K-Means, where the K of the K-Means can be computed using a Bayesian Information Criterion (BICk), for example, to determine the smallest value of K that meets system requirements. Any other criterion for K can be used. The K-Means clustering technique can be used to group one or more events into various respective categories.

The flow 900 continues with characterizing cluster profiles 940. The profiles can include a variety of facial expressions such as smiles, asymmetric smiles, eyebrow raisers, eyebrow lowerers, etc. The profiles can be related to a given event. For example, a humorous video can be displayed in the web-based framework and the video data of people who have opted in can be collected. The characterization of the collected and analyzed video can depend in part on the number of smiles that occurred at various points throughout the humorous video. The number of smiles resulting from people viewing a humorous video can be compared to various demographic groups, where the groups can be formed based on geographic location, age, ethnicity, gender, and so on. Similarly, the characterization can be performed on collected and analyzed videos of people viewing a news presentation. The characterized cluster profiles can be further analyzed based on demographic data. Various steps in the flow 900 may be changed in order, repeated, omitted, or the like without departing from the disclosed concepts. Various embodiments of the flow 900 can be included in a computer program product embodied in a non-transitory computer readable medium that includes code executable by one or more processors. Various embodiments of the flow 900, or portions thereof, can be included on a semiconductor chip and implemented in special purpose logic, programmable logic, and so on. Various embodiments of flow 900, or portions thereof, can be used for a processor-implemented method for robotic control using profiles.

Figure 10:
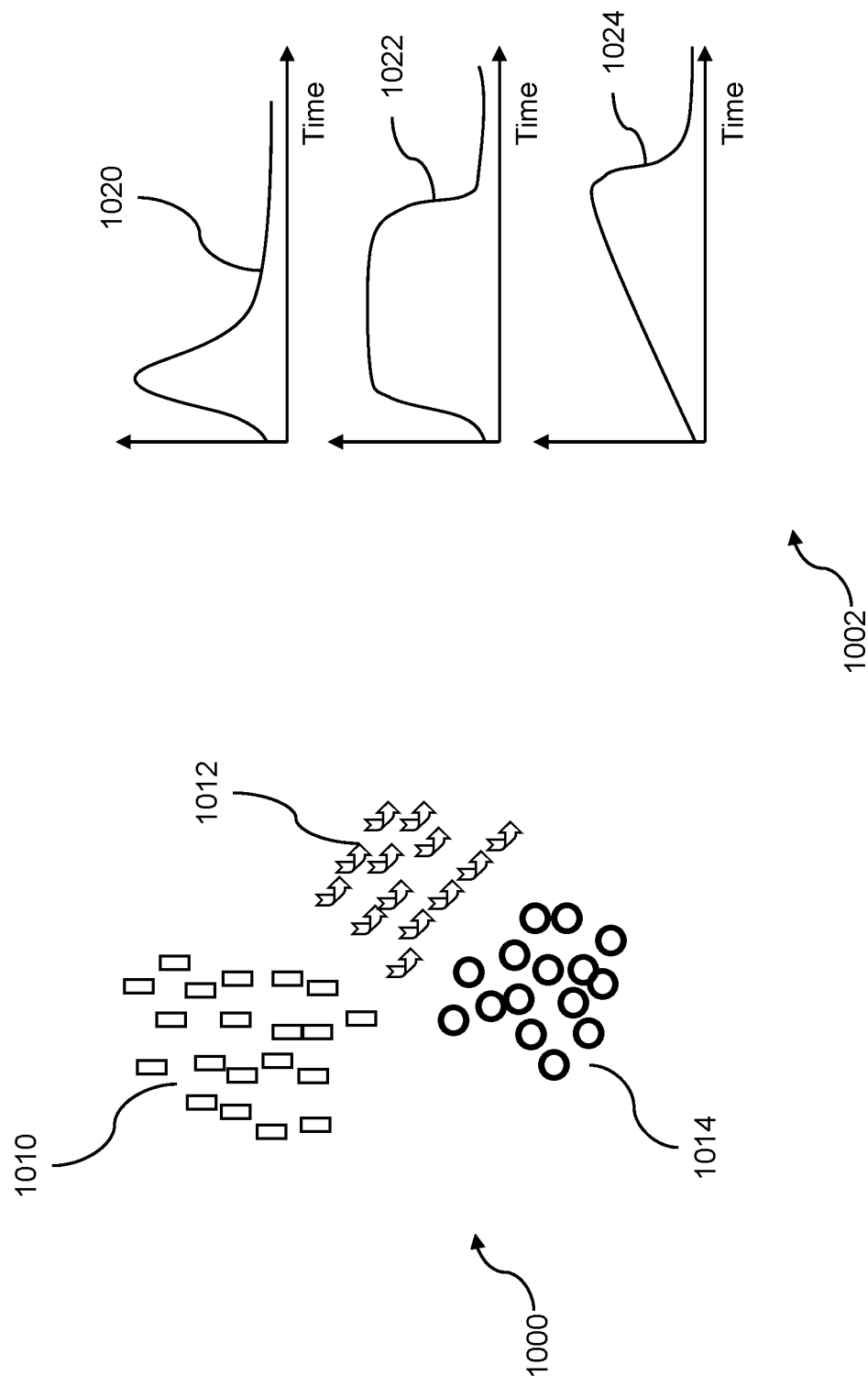
FIG. 10 shows unsupervised clustering of features and characterizations of cluster profiles.

FIG. 10 shows unsupervised clustering of features and characterizations of cluster profiles. The clustering can be accomplished as part of a deep learning effort. The clustering of features and characterizations of cluster profiles can be performed for images and audio collected of an individual. The collected images can be analyzed for cognitive states and/or facial expressions. Deep learning can enable robotic control using profiles. Cognitive state data for an individual is obtained. A cognitive state profile for the individual is learned using the cognitive state data that was obtained. Further cognitive state data for the individual is collected. The further cognitive state data is compared with the cognitive state profile. Stimuli are provided by a robot to the individual based on the comparing. Audio and a plurality of images can be obtained of an individual viewing an electronic display. A face can be identified in an image, based on the use of classifiers. The plurality of images can be evaluated to determine cognitive states and/or facial expressions of the individual. The audio can include voice data. The audio can include singing. In embodiments, the obtaining includes collecting voice data and augmenting the cognitive state data with the voice data. The voice data can be evaluated. In embodiments, evaluating can include evaluating the voice data for timbre, prosody, vocal register, vocal resonance, pitch, loudness, speech rate, or language content. The voice data, which can include audio data, can provide context for the first robot.

Features including samples of facial data can be clustered using unsupervised clustering. Various clusters can be formed, which include similar groupings of facial data observations. The example 1000 shows three clusters: a first cluster 1010, a second cluster 1012, and a third cluster 1014. The clusters can be based on video collected from people who have opted in to video collection. When the data collected is captured using a web-based framework, the data collection can be performed on a grand scale, including hundreds, thousands, or even more participants who can be situated locally and/or across a wide geographic area. Unsupervised clustering is a technique that can be used to process the large amounts of captured facial data and to identify groupings of similar observations. The unsupervised clustering can also be used to characterize the groups of similar observations. The characterizations can include identifying behaviors of the participants. The characterizations can be based on identifying facial expressions and facial action units of the participants. Some behaviors and facial expressions can include faster or slower onsets, faster or slower offsets, longer or shorter durations, etc. The onsets, offsets, and durations can all correlate to time. The data clustering that results from the unsupervised clustering can support data labeling. The labeling can include FACS coding. The clusters can be partially or totally based on a facial expression resulting from participants viewing a video presentation, where the video presentation can be an advertisement, a political message, educational material, a public service announcement, and so on. The clusters can be correlated with demographic information, where the demographic information can include educational level, geographic location, age, gender, income level, and so on.

The cluster profiles 1002 can be generated based on the clusters that can be formed from unsupervised clustering, with time shown on the x-axis and intensity or frequency shown on the y-axis. The cluster profiles can be based on captured facial data including facial expressions. The cluster profile 1020 can be based on the cluster 1010, the cluster profile 1022 can be based on the cluster 1012, and the cluster profile 1024 can be based on the cluster 1014. The cluster profiles 1020, 1022, and 1024 can be based on smiles, smirks, frowns, or any other facial expression. The emotional states of the people who have opted in to video collection can be inferred by analyzing the clustered facial expression data. The cluster profiles can be plotted with respect to time and can show a rate of onset, a duration, and an offset (rate of decay). Other time-related factors can be included in the cluster profiles. The cluster profiles can be correlated with demographic information, as described above. The cluster profiles can be used in determining weights and image classifiers that can be deployed to a client device. The weights and image classifiers can be used to infer an emotion metric.

Figure 11A:
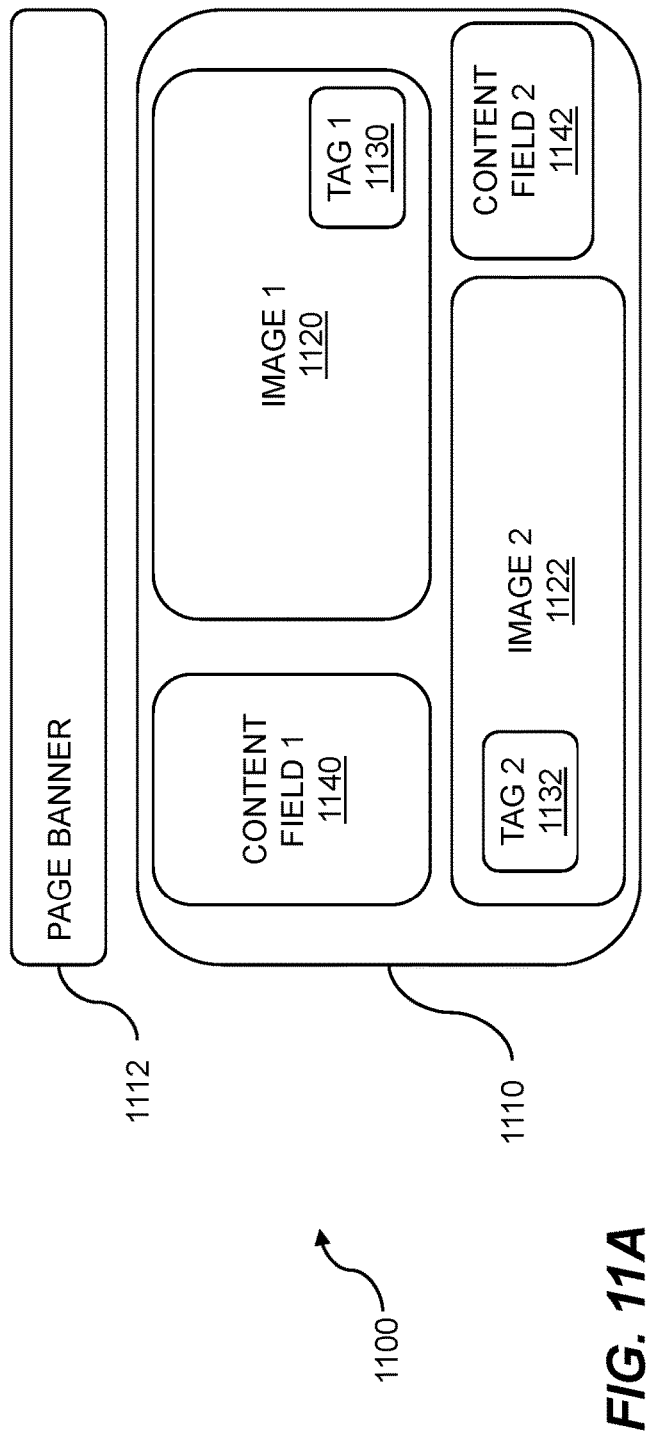
FIG. 11A shows example tags embedded in a webpage.

FIG. 11A shows example tags embedded in a webpage. As the tags that are embedded in the webpage are encountered, cognitive state data including facial data and audio data for an individual can be collected and analyzed. Image and audio collection can enable interaction with a robot that is based on a profile. Profiles can be used for robotic control. Cognitive state data for an individual is obtained. A cognitive state profile for the individual is learned using the cognitive state data that was obtained. Further cognitive state data for the individual is collected. The further cognitive state data is compared with the cognitive state profile.

Stimuli are provided by a robot to the individual based on the comparing. A webpage 1100 can include a page body 1110, a page banner 1112, and so on. The page body can include one or more objects, where the objects can include text, images, videos, audio, etc. The example page body 1110 shown includes a first image, image 1 1120; a second image, image 2 1122; a first content field, content field 1 1140; and a second content field, content field 2 1142. In practice, the page body 1110 can contain any number of images and content fields and can include one or more videos, one or more audio presentations, and so on. The page body can include embedded tags, such as tag 1 1130 and tag 2 1132. In the example shown, tag 1 1130 is embedded in image 1 1120, and tag 2 1132 is embedded in image 2 1122. In embodiments, any number of tags is embedded. Tags can also be embedded in content fields, in videos, in audio presentations, etc. When a user mouses over a tag or clicks on an object associated with a tag, the tag can be invoked. For example, when the user mouses over tag 1 1130, tag 1 1130 can then be invoked. Invoking tag 1 1130 can include enabling a camera coupled to a user's device and capturing one or more images of the user as the user views an image, a media presentation (or digital experience), and so on. In a similar manner, when the user mouses over tag 2 1132, tag 2 1132 can be invoked. Invoking tag 2 1132 can also include enabling the camera and capturing images of the user. In other embodiments, other actions are taken based on invocation of the one or more tags. For example, invoking an embedded tag can trigger determining weights and image classifiers and deploying the weights and image classifiers to a client device. In another example, invoking an embedded tag can initiate an analysis technique, post to social media, award the user a coupon or another prize, initiate cognitive state analysis, perform emotion analysis, and so on.

Figure 11B:
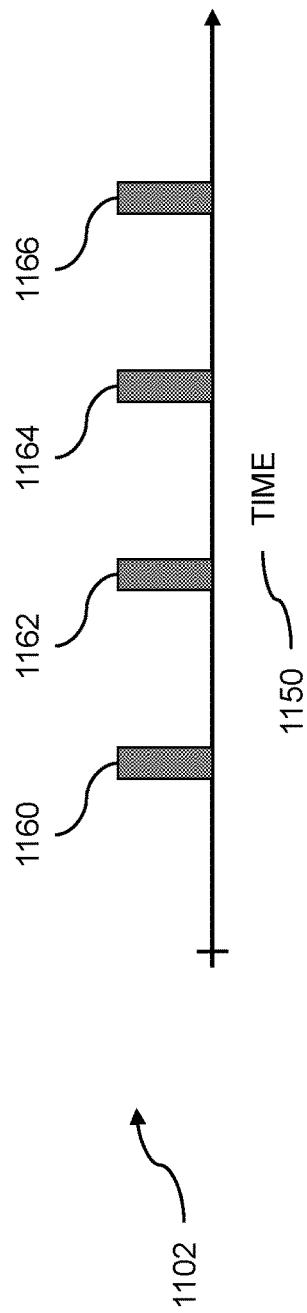
FIG. 11B shows an example of invoking tags to collect images.

FIG. 11B shows an example of invoking tags to collect images. In embodiments, the invoking tags can be used to collect audio. As stated above, a media presentation can be a video, a webpage, and so on. Tags can be used to enable robotic control using profiles. Cognitive state data for an individual is obtained. A cognitive state profile for the individual is learned using the cognitive state data that was obtained. Further cognitive state data for the individual is collected. The further cognitive state data is compared with the cognitive state profile. Stimuli are provided by a robot to the individual based on the comparing. A video 1102 can include one or more embedded tags, such as a tag 1160, another tag 1162, a third tag 1164, a fourth tag 1166, and so on. In practice, any number of tags can be included in the media presentation, a digital presentation, and so on. The one or more tags can be invoked during the media presentation. The collection of the invoked tags can occur over time as represented by a timeline 1150. When a tag is encountered in the media presentation, the tag can be invoked. For example, when the tag 1160 is encountered, invoking the tag can enable a camera coupled to a user device and can capture one or more images of the user viewing the media presentation. Invoking a tag can depend on opt-in by the user. For example, if a user has agreed to participate in a study by indicating an opt-in, then the camera coupled to the user's device can be enabled and one or more images of the user can be captured. If the user has not agreed to participate in the study and has not indicated an opt-in, then invoking the tag 1160 does not enable the camera to capture images of the user during the media presentation. The user can indicate an opt-in for certain types of participation, where opting in can be dependent on specific content in the media presentation.

Figure 12:
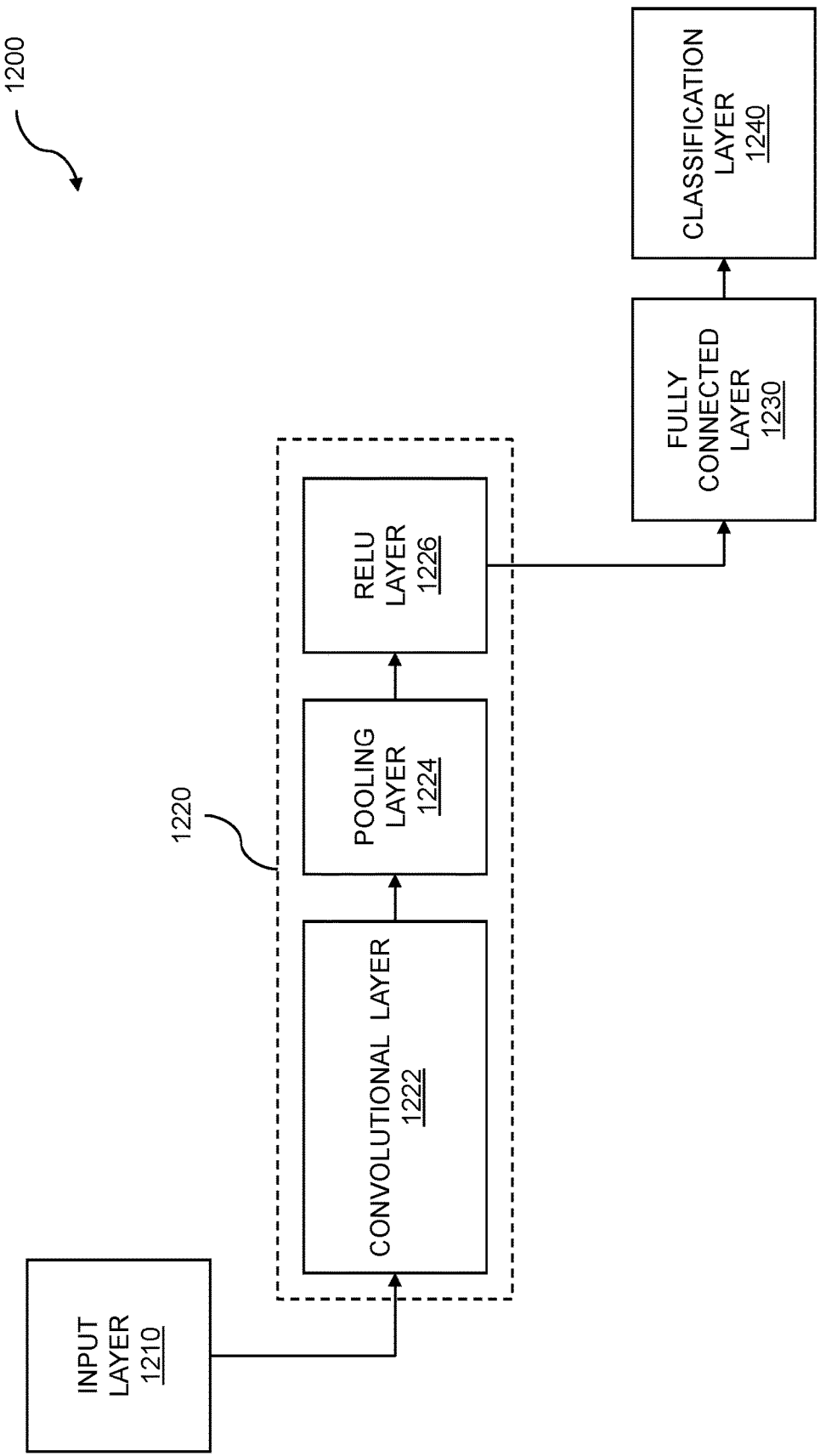
FIG. 12 is an example showing a convolutional neural network.

FIG. 12 is an example showing a convolutional neural network (CNN). The convolutional neural network can be used for deep learning, where the deep learning can be applied to robotic control using profiles. A robot can be a smart toy interacting with an individual. The smart toy interaction can be between a child, a patient, a student, or other individuals and the smart toy. Cognitive state data, including facial data and audio data, is obtained from an individual and used to learn a cognitive state profile. Further cognitive state data is collected and compared with the cognitive state profile. The comparing is used as a basis for providing stimuli by a robot smart toy.

Emotion analysis is a very complex task. Understanding and evaluating moods, emotions, mental states, or cognitive states, requires a nuanced evaluation of facial expressions or other cues generated by people. Cognitive state analysis is important in many areas such as research, psychology, business, intelligence, law enforcement, and so on. The understanding of cognitive states can be useful for a variety of business purposes, such as improving marketing analysis, assessing the effectiveness of customer service interactions and retail experiences, and evaluating the consumption of content such as movies and videos. Identifying points of frustration in a customer transaction can allow a company to take action to address the causes of the frustration. By streamlining processes, key performance areas such as customer satisfaction and customer transaction throughput can be improved, resulting in increased sales and revenues. In a content scenario, producing compelling content that achieves the desired effect (e.g. fear, shock, laughter, etc.) can result in increased ticket sales and/or increased advertising revenue. If a movie studio is producing a horror movie, it is desirable to know if the scary scenes in the movie are achieving the desired effect. By conducting tests in sample audiences, and analyzing faces in the audience, a computer-implemented method and system can process thousands of faces to assess the cognitive state at the time of the scary scenes. In many ways, such an analysis can be more effective than surveys that ask audience members questions, since audience members may consciously or subconsciously change answers based on peer pressure or other factors. However, spontaneous facial expressions can be more difficult to conceal. Thus, by analyzing facial expressions en masse in real time, important information regarding the general cognitive state of the audience can be obtained.

Analysis of facial expressions is also a complex task. Image data, where the image data can include facial data, can be analyzed to identify a range of facial expressions. The facial expressions can include a smile, frown, smirk, and so on. The image data and facial data can be processed to identify the facial expressions. The processing can include analysis of expression data, action units, gestures, mental states, cognitive states, physiological data, and so on. Facial data as contained in the raw video data can include information on one or more of action units, head gestures, smiles, brow furrows, squints, lowered eyebrows, raised eyebrows, attention, and the like. The action units can be used to identify smiles, frowns, and other facial indicators of expressions. Gestures can also be identified, and can include a head tilt to the side, a forward lean, a smile, a frown, as well as many other gestures. Other types of data including the physiological data can be collected, where the physiological data can be obtained using a camera or other image capture device, without contacting the person or persons. Respiration, heart rate, heart rate variability, perspiration, temperature, and other physiological indicators of cognitive state can be determined by analyzing the images and video data.

Deep learning is a branch of machine learning which seeks to imitate in software the activity which takes place in layers of neurons in the neocortex of the human brain. This imitative activity can enable software to "learn" to recognize and identify patterns in data, where the data can include digital forms of images, sounds, and so on. The deep learning software is used to simulate the large array of neurons of the neocortex. This simulated neocortex, or artificial neural network, can be implemented using mathematical formulas that are evaluated on processors. With the ever-increasing capabilities of the processors, increasing numbers of layers of the artificial neural network can be processed.

Deep learning applications include processing of image data, audio data, and so on. Image data applications include image recognition, facial recognition, etc. Image data applications can include differentiating dogs from cats, identifying different human faces, and the like. The image data applications can include identifying cognitive states, moods, mental states, emotional states, and so on, from the facial expressions of the faces that are identified. Audio data applications can include analyzing audio such as ambient room sounds, physiological sounds such as breathing or coughing, noises made by an individual such as tapping and drumming, voices, and so on. The voice data applications can include analyzing a voice for timbre, prosody, vocal register, vocal resonance, pitch, loudness, speech rate, or language content. The voice data analysis can be used to determine one or more cognitive states, moods, mental states, emotional states, etc.

The artificial neural network, such as a convolutional neural network which forms the basis for deep learning, is based on layers. The layers can include an input layer, a convolutional layer, a fully connected layer, a classification layer, and so on. The input layer can receive input data such as image data, where the image data can include a variety of formats including pixel formats. The input layer can then perform processing such as identifying boundaries of the face, identifying landmarks of the face, extracting features of the face, and/or rotating a face within the plurality of images. The convolutional layer can represent an artificial neural network such as a convolutional neural network. A convolutional neural network can contain a plurality of hidden layers within it. A convolutional layer can reduce the amount of data feeding into a fully connected layer. The fully connected layer processes each pixel/data point from the convolutional layer. A last layer within the multiple layers can provide output which is indicative of cognitive state. The last layer of the convolutional neural network can be the final classification layer. The output of the final classification layer can be indicative of the cognitive states of faces within the images that are provided to the input layer.

Deep networks including deep convolutional neural networks can be used for facial expression parsing. A first layer of the deep network includes multiple nodes, where each node represents a neuron within a neural network. The first layer can receive data from an input layer. The output of the first layer can feed to a second layer, where the latter layer also includes multiple nodes. A weight can be used to adjust the output of the first layer which is being input to the second layer. Some layers in the convolutional neural network can be hidden layers. The output of the second layer can feed to a third layer. The third layer can also include multiple nodes. A weight can adjust the output of the second layer which is being input to the third layer. The third layer may be a hidden layer. Outputs of a given layer can be fed to next layer. Weights adjust the output of one layer as it is fed to the next layer. When the final layer is reached, the output of the final layer can be a facial expression, a cognitive state, a mental state, a characteristic of a voice, and so on. The facial expression can be identified using a hidden layer from the one or more hidden layers. The weights can be provided on inputs to the multiple layers to emphasize certain facial features within the face. The convolutional neural network can be trained to identify facial expressions, voice characteristics, etc. The training can include assigning weights to inputs on one or more layers within the multilayered analysis engine. One or more of the weights can be adjusted or updated during training. The assigning weights can be accomplished during a feed-forward pass through the multilayered neural network. In a feed-forward arrangement, the information moves forward from the input nodes, through the hidden nodes, and on to the output nodes. Additionally, the weights can be updated during a backpropagation process through the multilayered analysis engine.

Returning to the figure, FIG. 12 is an example showing a convolutional neural network 1200. The convolutional neural network can be used for deep learning, where the deep learning can be applied to avatar image animation using translation vectors. The deep learning system can be accomplished using a convolutional neural network or other techniques. The deep learning can accomplish facial recognition and analysis tasks. The network includes an input layer 1210. The input layer 1210 receives image data. The image data can be input in a variety of formats, such as JPEG, TIFF, BMP, and GIF. Compressed image formats can be decompressed into arrays of pixels, wherein each pixel can include an RGB tuple. The input layer 1210 can then perform processing such as identifying boundaries of the face, identifying landmarks of the face, extracting features of the face, and/or rotating a face within the plurality of images.

The network includes a collection of intermediate layers 1220. The multilayered analysis engine can include a convolutional neural network. Thus, the intermediate layers can include a convolutional layer 1222. The convolutional layer 1222 can include multiple sublayers, including hidden layers, within it. The output of the convolutional layer 1222 feeds into a pooling layer 1224. The pooling layer 1224 performs a data reduction, which makes the overall computation more efficient. Thus, the pooling layer reduces the spatial size of the image representation to reduce the number of parameters and computation in the network. In some embodiments, the pooling layer is implemented using filters of size 2×2, applied with a stride of two samples for every depth slice along both width and height, resulting in a reduction of 75-percent of the downstream node activations. The pooling layer 1224 of the multilayered analysis engine can comprise a max pooling layer. Thus, in embodiments, the pooling layer is a max pooling layer, in which the output of the filters is based on a maximum of the inputs. For example, with a 2×2 filter, the output is based on a maximum value from the four input values. In other embodiments, the pooling layer is an average pooling layer or L2-norm pooling layer. Various other pooling schemes are possible.

The intermediate layers can include a Rectified Linear Units, or RELU, layer 1226. The output of the pooling layer 1224 can be input to the RELU layer 1226. In embodiments, the RELU layer implements an activation function such as $f(x)=\max(0,x)$, thus providing an activation with a threshold at zero. In some embodiments, the RELU layer 1226 is a leaky RELU layer. In this case, instead of the activation function providing zero when x<0, a small negative slope is used, resulting in an activation function such as $f(x)=1(x<0)(\alpha x)+1(x>=0)(x)$. This can reduce the risk of "dying RELU" syndrome, where portions of the network can be "dead" with nodes/neurons that do not activate across the training dataset. The image analysis can comprise training a multilayered analysis engine using the plurality of images, wherein the multilayered analysis engine can include multiple layers that include one or more convolutional layers 1222 and one or more hidden layers, and wherein the multilayered analysis engine can be used for emotional analysis.

The example 1200 includes a fully connected layer 1230. The fully connected layer 1230 processes each pixel/data point from the output of the collection of intermediate layers 1220. The fully connected layer 1230 takes all neurons in the previous layer and connects them to every single neuron it has. The output of the fully connected layer 1230 provides input to a classification layer 1240. The output of the classification layer 1240 provides a facial expression and/or cognitive state as its output. Thus, a multilayered analysis engine such as the one depicted in FIG. 12 processes image data using weights, models the way the human visual cortex performs object recognition and learning, and is effective for analysis of image data to infer facial expressions and cognitive states.

Machine learning for generating parameters, analyzing data such as facial data and audio data, and so on, can be based on a variety of computational techniques. Generally, machine learning can be used for constructing algorithms and models. The constructed algorithms, when executed, can be used to make a range of predictions relating to data. The predictions can include whether an object in an image is a face, a box, or a puppy, whether a voice is female, male, or robotic, whether a message is legitimate email or a "spam" message, and so on. The data can include unstructured data and can be of large quantity. The algorithms that can be generated by machine learning techniques are particularly useful to data analysis because the instructions that comprise the data analysis technique do not need to be static. Instead, the machine learning algorithm or model, generated by the machine learning technique, can adapt. Adaptation of the learning algorithm can be based on a range of criteria such as success rate, failure rate, and so on. A successful algorithm is one that can adapt—or learn—as more data is presented to the algorithm. Initially, an algorithm can be "trained" by presenting it with a set of known data (supervised learning). Another approach, called unsupervised learning, can be used to identify trends and patterns within data. Unsupervised learning is not trained using known data prior to data analysis.

Reinforced learning is an approach to machine learning that is inspired by behaviorist psychology. The underlying premise of reinforced learning (also called reinforcement learning) is that software agents can take actions in an environment. The actions that are taken by the agents should maximize a goal such as a "cumulative reward". A software agent is a computer program that acts on behalf of a user or other program. The software agent is implied to have the authority to act on behalf of the user or program. The actions taken are decided by action selection to determine what to do next. In machine learning, the environment in which the agents act can be formulated as a Markov decision process (MDP). The MDPs provide a mathematical framework for modeling of decision making in environments where the outcomes can be partly random (stochastic) and partly under the control of the decision maker. Dynamic programming techniques can be used for reinforced learning algorithms.

Reinforced learning is different from supervised learning in that correct input/output pairs are not presented, and suboptimal actions are not explicitly corrected. Rather, on-line or computational performance is the focus. On-line performance includes finding a balance between exploration of new (uncharted) territory or spaces, and exploitation of current knowledge. That is, there is a tradeoff between exploration and exploitation.

Machine learning based on reinforced learning adjusts or learns based on learning an action, a combination of actions, and so on. An outcome results from taking an action. Thus, the learning model, algorithm, etc., learns from the outcomes that result from taking the action or combination of actions. The reinforced learning can include identifying positive outcomes, where the positive outcomes are used to adjust the learning models, algorithms, and so on. A positive outcome can be dependent on a context. When the outcome is based on a mood, emotional state, mental state, cognitive state, etc., of an individual, then a positive mood, emotion, mental state, or cognitive state can be used to adjust the model and algorithm. Positive outcomes can include a person being more engaged, where engagement is based on affect, the person spending more time playing an online game or navigating a webpage, the person converting by buying a product or service, and so on. The reinforced learning can be based on exploring a solution space and adapting the model, algorithm, etc., based on outcomes of the exploration. When positive outcomes are encountered, the positive outcomes can be reinforced by changing weighting values within the model, algorithm, etc. Positive outcomes may result in increasing weighting values. Negative outcomes can also be considered, where weighting values may be reduced or otherwise adjusted.

Figure 13:
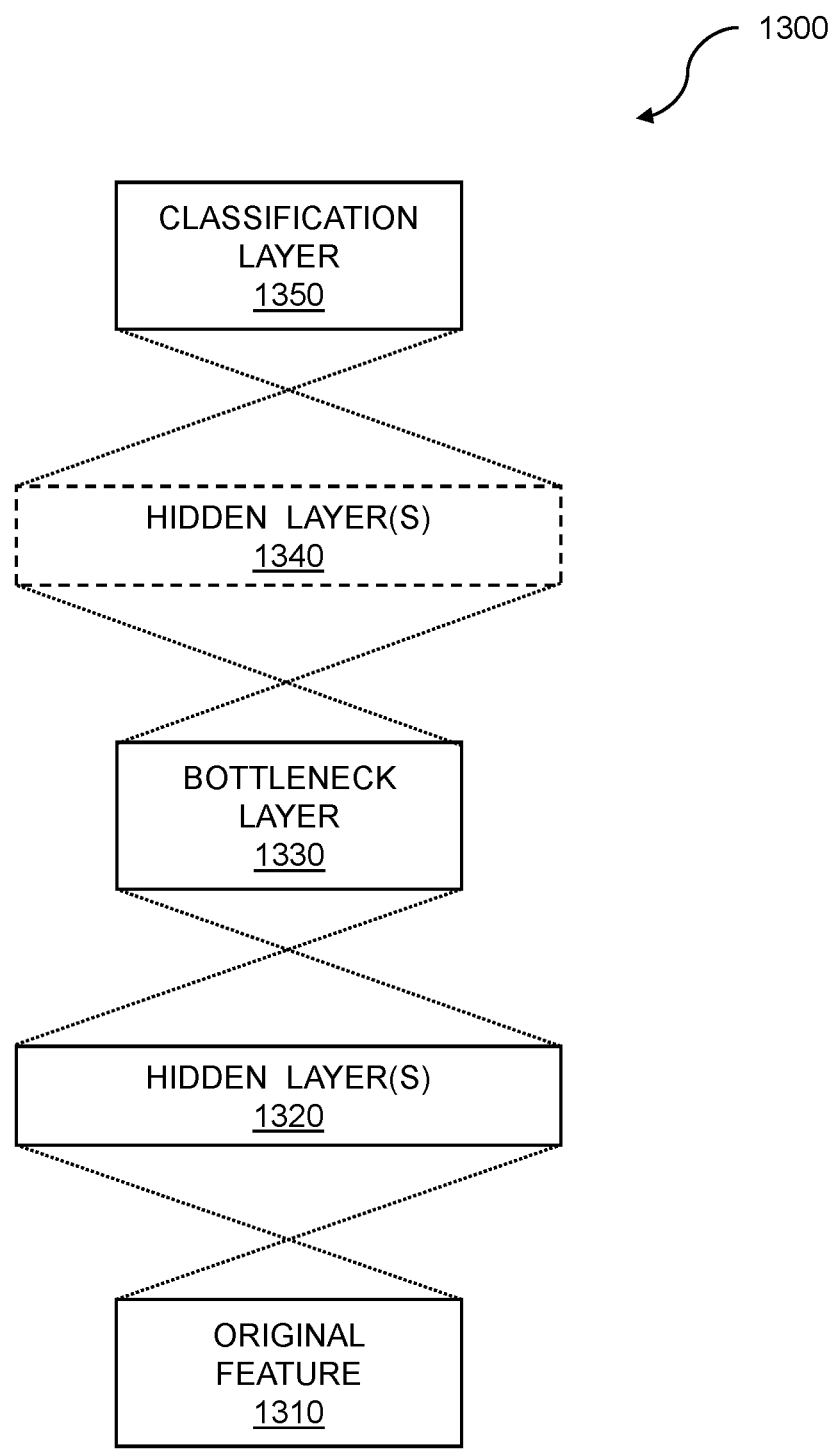
FIG. 13 illustrates a bottleneck layer within a deep learning environment.

FIG. 13 illustrates a bottleneck layer within a deep learning environment. A bottleneck layer can be a layer within a deep neural network. The bottleneck layer and the deep neural network can be used for robotic control using profiles. Cognitive state data for an individual is obtained. A cognitive state profile for the individual is learned using the cognitive state data that was obtained. Further cognitive state data for the individual is collected. The further cognitive state data is compared with the cognitive state profile. Stimuli are provided by a robot to the individual based on the comparing. The stimuli provided by the robot can include visual, auditory, or haptic stimuli, and can be used for learning, reinforcement for an educational effort, and the like.

Layers of a deep neural network can include a bottleneck layer within a deep learning environment 1300. A bottleneck layer can be used for a variety of applications such as facial recognition, voice recognition, cognitive state recognition, emotional state recognition, and so on. The deep neural network in which the bottleneck layer is located can include a plurality of layers. The plurality of layers can include an original feature layer 1310. A feature such as an image feature can include points, edges, objects, boundaries between and among regions, properties, and so on. A feature such as a voice feature can include timbre, prosody, vocal register, vocal resonance, pitch, loudness, speech rate, or language content, etc. The deep neural network can include one or more hidden layers 1320. The one or more hidden layers can include nodes, where the nodes can include nonlinear activation functions and other techniques. The bottleneck layer can be a layer that learns translation vectors to transform a neutral face to an emotional or expressive face. In some embodiments, the translation vectors can transform a neutral sounding voice to an emotional or expressive voice. Specifically, activations of the bottleneck layer determine how the transformation occurs. A single bottleneck layer can be trained to transform a neutral face or voice to a different emotional face or voice. In some cases, an individual bottleneck layers can be trained for a transformation pair. At runtime, once the user's emotion has been identified and an appropriate response to it can be determined (mirrored or complementary), the trained bottleneck layer can be used to perform the needed transformation.

The deep neural network can include a bottleneck layer 1330. The bottleneck layer can include a fewer number of nodes than the one or more preceding hidden layers. The bottleneck layer can create a constriction in the deep neural network or other network. The bottleneck layer can force information that is pertinent to a classification, for example, into a low dimensional representation. The bottleneck features can be extracted using an unsupervised technique. In other embodiments, the bottleneck features can be extracted in a supervised manner. The supervised technique can include training the deep neural network with a known dataset. The features can be extracted from an autoencoder such as a variational autoencoder, a generative autoencoder, and so on. The deep neural network can include hidden layers 1340. The count of the hidden layers can include zero hidden layers, one hidden layer, a plurality of hidden layers, and so on. The hidden layers following the bottleneck layer can include more nodes than the bottleneck layer. The deep neural network can include a classification layer 1350. The classification layer can be used to identify the points, edges, objects, boundaries, and so on, described above. The classification layer can be used to identify cognitive states, mental states, emotional states, moods, and the like. The output of the final classification layer can be indicative of the emotional states of faces within the images, where the images can be processed using the deep neural network.

Figure 14:
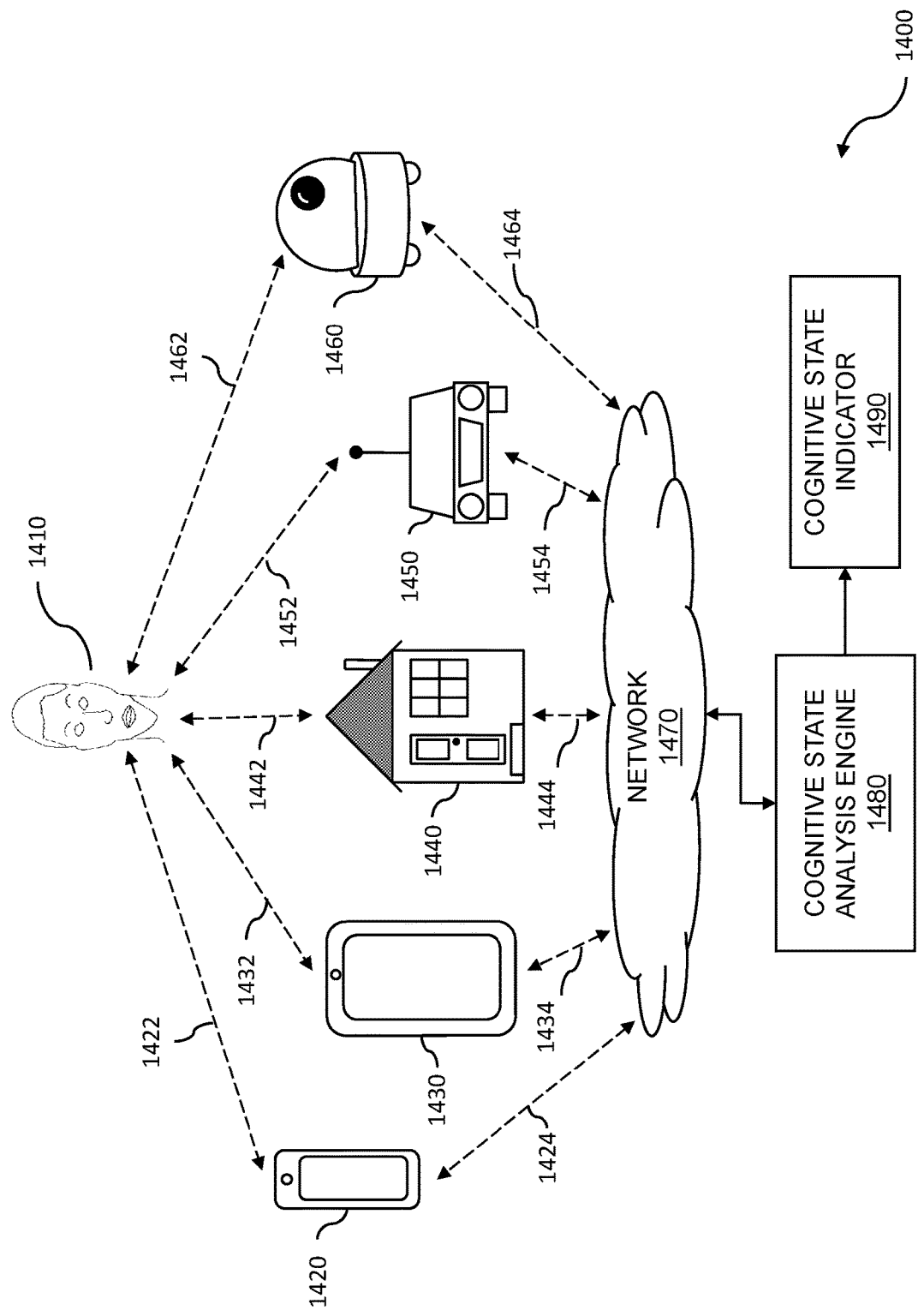
FIG. 14 shows data collection including devices and locations.

FIG. 14 shows data collection including devices and locations 1400. Data collection can enable interaction with a robot that is based on a profile. Profiles can be used for robotic control. Cognitive state data for an individual is obtained. A cognitive state profile for the individual is learned using the cognitive state data that was obtained. Further cognitive state data for the individual is collected. The further cognitive state data is compared with the cognitive state profile. Stimuli are provided by a robot to the individual based on the comparing. Stimuli, such as positive reinforcement for an education effort, can be provided by a robot smart toy. The multiple mobile devices, vehicles, and locations, can be used separately or in combination to collect video data and audio data on a user 1410. While one person is shown, the video data and audio data can be collected on multiple people. A user 1410 can be observed as she or he is performing a task, experiencing an event, viewing a media presentation, and so on. The user 1410 can be shown one or more media presentations, political presentations, social media, or another form of displayed media. The one or more media presentations can be shown to a plurality of people. The media presentations can be displayed on an electronic display coupled to a client device. The data collected on the user 1410 or on a plurality of users can be in the form of one or more videos, video frames, still images, audio tracks, audio segments, etc. The plurality of videos and audio can be of people who are experiencing different situations. Some example situations can include the user or plurality of users being exposed to TV programs, movies, video clips, social media, social sharing, and other such media. The situations could also include exposure to media such as advertisements, political messages, news programs, and so on. As noted before, video data can be collected on one or more users in substantially identical or different situations and viewing either a single media presentation or a plurality of presentations. The data collected on the user 1410 can be analyzed and viewed for a variety of purposes including expression analysis, cognitive state analysis, mental state analysis, emotional state analysis, voice analysis, and so on. The electronic display can be on a smartphone 1420 as shown, a tablet computer 1430, a personal digital assistant, a television, a mobile monitor, or any other type of electronic device. In one embodiment, expression data and voice data are collected on a mobile device such as a smartphone 1420, a tablet computer 1430, a laptop computer, or a watch. Thus, the multiple sources can include at least one mobile device, such as a smartphone 1420 or a tablet computer 1430, or a wearable device such as a watch or glasses (not shown). A mobile device can include a front-facing camera and/or a rear-facing camera that can be used to collect expression data. Sources of expression data can include a webcam, a phone camera, a tablet camera, a wearable camera, and a mobile camera. A wearable camera can comprise various camera devices, such as a watch camera. In addition to using client devices for data collection from the user 1410, data can be collected in a house 1440 using a web camera or the like; in a vehicle 1450 using a web camera, client device, etc.; by a social robot 1460, and so on.

As the user 1410 is monitored, the user 1410 might move due to the nature of the task, boredom, discomfort, distractions, or for another reason. As the user moves, the camera with a view of the user's face can be changed. Thus, as an example, if the user 1410 is looking in a first direction, the line of sight 1422 from the smartphone 1420 is able to observe the user's face, but if the user is looking in a second direction, the line of sight 1432 from the tablet computer 1430 is able to observe the user's face. Furthermore, in other embodiments, if the user is looking in a third direction, the line of sight 1442 from a camera in the house 1440 is able to observe the user's face, and if the user is looking in a fourth direction, the line of sight 1452 from the camera in the vehicle 1450 is able to observe the user's face. If the user is looking in a fifth direction, the line of sight 1462 from the social robot 1460 is able to observe the user's face. If the user is looking in a sixth direction, a line of sight from a wearable watch-type device, with a camera included on the device, is able to observe the user's face. In other embodiments, the wearable device is another device, such as an earpiece with a camera, a helmet or hat with a camera, a clip-on camera attached to clothing, or any other type of wearable device with a camera or other sensor for collecting expression data. The user 1410 can also use a wearable device including a camera for gathering contextual information and/or collecting expression data on other users. Because the user 1410 can move her or his head, the facial data can be collected intermittently when she or he is looking in a direction of a camera. In some cases, multiple people can be included in the view from one or more cameras, and some embodiments include filtering out faces of one or more other people to determine whether the user 1410 is looking toward a camera. All or some of the expression data can be continuously or sporadically available from the various devices and other devices.

The captured video data and audio data can include facial expressions, voice data, etc., and can be transferred over the network 1470. The smartphone 1420 can share video and audio using a link 1424, the tablet computer 1430 using a link 1434, the house 1440 using a link 1444, the vehicle 1450 using a link 1454, and the social robot 1460 using a link 1464. The links 1424, 1434, 1444, 1454, and 1464 can be wired, wireless, and hybrid links. The captured video data and audio data, including facial expressions and voice data, can be analyzed on a cognitive state analysis engine 1480, on a computing device such as the video capture device, or on another separate device. The analysis could take place on one of the mobile devices discussed above, on a local server, on a remote server, and so on. In embodiments, some of the analysis takes place on the mobile device, while other analysis takes place on a server device. The analysis of the video data and the audio data can include the use of a classifier. The video data and audio data can be captured using one of the mobile devices discussed above and sent to a server or another computing device for analysis. However, the captured video data and audio data including facial expressions and voice data can also be analyzed on the device which performed the capturing. The analysis can be performed on a mobile device where the videos were obtained with the mobile device and wherein the mobile device includes one or more of a laptop computer, a tablet, a PDA, a smartphone, a wearable device, and so on. In another embodiment, the analyzing comprises using a classifier on a server or another computing device other than the capture device. The analysis data from the cognitive state analysis engine can be processed by a cognitive state indicator 1490. The cognitive state indicator 1490 can indicate cognitive states, mental states, moods, emotions, etc. In embodiments, the cognitive states can include of one or more of sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, sadness, poignancy, fatigue, drowsiness, or mirth. Analysis can include audio evaluation for non-speech vocalizations including yawning, sighing, groaning, laughing, singing, snoring, and the like.

Figure 15:
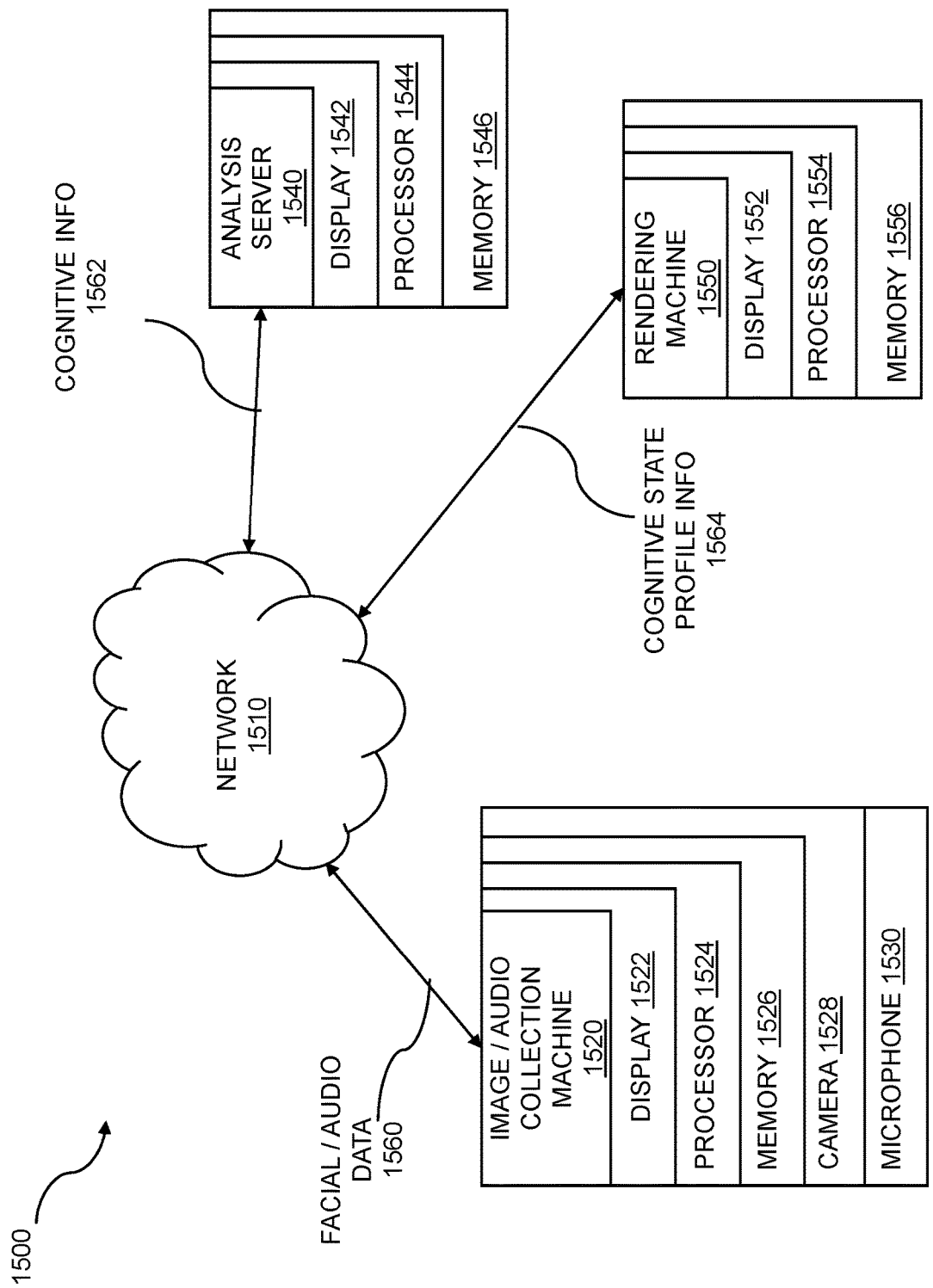
FIG. 15 is a system for robot interaction.

FIG. 15 is a system for robot interaction. A system 1500 for robotic control using profiles is shown. The system 1500 can provide a processor-implemented method for robotic control comprising: obtaining, using a first computing device, cognitive state data for an individual including facial data for the individual; learning, using a second computing device, a cognitive state profile for the individual using the cognitive state data that was obtained; collecting further cognitive state data for the individual; comparing the further cognitive state data with the cognitive state profile; and providing stimuli by a first robot to the individual based on the comparing.

The system 1500 can include one or more image and audio collection machines 1520 linked to an analysis server 1540 and a rendering machine 1550 via the network 1510. The network can include a wired network, a wireless network, a hybrid network, the Internet, or another computer network. The network can be a wired network, a wireless network, a hybrid network, and so on. Facial and audio data 1560 can be transferred to the analysis server 1540 through the network 1510, for example. The example image and audio collection machine 1520 shown comprises one or more processors 1524 coupled to a memory 1526 which can store and retrieve instructions, a display 1522, and a camera 1528. In embodiments, the image and audio collection machine includes a microphone 1530 or other audio capture apparatus. The camera 1528 can include a webcam, a video camera, a still camera, a thermal imager, a CCD device, a phone camera, a three-dimensional camera, a depth camera, a light field camera, multiple webcams used to show different views of a person, or any other type of image capture technique that can allow captured data to be used in an electronic system. The memory 1526 can be used for storing instructions; image data, cognitive state data, and facial data; voice data and audio data; one or more classifiers; one or more cognitive state profiles; and so on. The display 1522 can be any electronic display, including but not limited to, a computer display, a laptop screen, a netbook screen, a tablet computer screen, a smartphone display, a mobile device display, a remote with a display, a television, a projector, or the like.

The analysis server 1540 can include one or more processors 1544 coupled to a memory 1546 which can store and retrieve instructions, and it can include a display 1542. The analysis server 1540 can receive cognitive information 1562 and analyze the image and audio data. The analysis server 1540 can use facial and audio data 1560 received from the image and audio data collection machine 1520 to produce cognitive state profile information 1564. In some embodiments, the analysis server 1540 receives facial and audio data from a plurality of image and audio data collection machines, aggregates the facial and audio data, processes the facial and audio data or the aggregated facial and audio data, and so on. In some embodiments, the analysis server 1540 captures cognitive state data from the facial and audio data 1560 and infers cognitive states from the cognitive state data.

The rendering machine 1550 can include one or more processors 1554 coupled to a memory 1556 which can store and retrieve instructions and data, and it can include a display 1552. The rendering of cognitive states based on cognitive state profile information 1564 can occur on the rendering machine 1550 or on a different platform from the rendering machine 1550. In embodiments, the rendering based cognitive state profile information data occurs on the image and audio data collection machine 1520 or on the analysis server 1540. As shown in the system 1500, the rendering machine 1550 can receive cognitive state profile information 1564 via the network 1510, the Internet, or another network, from the image and audio data collection machine 1520, from the analysis server 1540, or from both. The rendering machine can include a visual display or any other appropriate display format.

In embodiments, the system 1500 comprises a computer system for robotic control comprising: a memory which stores instructions; one or more processors coupled to the memory wherein the one or more processors, when executing the instructions which are stored, are configured to: obtain cognitive state data for an individual including facial data for the individual; learn a cognitive state profile for the individual using the cognitive state data that was obtained; collect further cognitive state data for the individual; compare the further cognitive state data with the cognitive state profile; and provide stimuli by a first robot to the individual based on the comparing.

In embodiments, the system 1500 can include a computer program product embodied in a non-transitory computer readable medium for robotic control, the computer program product comprising code which causes one or more processors to perform operations of: obtaining cognitive state data for an individual including facial data for the individual; learning a cognitive state profile for the individual using the cognitive state data that was obtained; collecting further cognitive state data for the individual; comparing the further cognitive state data with the cognitive state profile; and providing stimuli by a first robot to the individual based on the comparing.

Each of the above methods may be executed on one or more processors on one or more computer systems. Embodiments may include various forms of distributed computing, client/server computing, and cloud-based computing. Further, it will be understood that the depicted steps or boxes contained in this disclosure's flow charts are solely illustrative and explanatory. The steps may be modified, omitted, repeated, or re-ordered without departing from the scope of this disclosure. Further, each step may contain one or more sub-steps. While the foregoing drawings and description set forth functional aspects of the disclosed systems, no particular implementation or arrangement of software and/or hardware should be inferred from these descriptions unless explicitly stated or otherwise clear from the context. All such arrangements of software and/or hardware are intended to fall within the scope of this disclosure.

The block diagrams and flowchart illustrations depict methods, apparatus, systems, and computer program products. The elements and combinations of elements in the block diagrams and flow diagrams, show functions, steps, or groups of steps of the methods, apparatus, systems, computer program products and/or computer-implemented methods. Any and all such functions—generally referred to herein as a "circuit," "module," or "system"—may be implemented by computer program instructions, by special-purpose hardware-based computer systems, by combinations of special purpose hardware and computer instructions, by combinations of general purpose hardware and computer instructions, and so on.

A programmable apparatus which executes any of the above-mentioned computer program products or computer-implemented methods may include one or more microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are neither limited to conventional computer applications nor the programmable apparatus that run them. To illustrate: the embodiments of the presently claimed invention could include an optical computer, quantum computer, analog computer, or the like. A computer program may be loaded onto a computer to produce a particular machine that may perform any and all of the depicted functions. This particular machine provides a means for carrying out any and all of the depicted functions.

Any combination of one or more computer readable media may be utilized including but not limited to: a non-transitory computer readable medium for storage; an electronic, magnetic, optical, electromagnetic, infrared, or semiconductor computer readable storage medium or any suitable combination of the foregoing; a portable computer diskette; a hard disk; a random access memory (RAM); a read-only memory (ROM), an erasable programmable read-only memory (EPROM, Flash, MRAM, FeRAM, or phase change memory); an optical fiber; a portable compact disc; an optical storage device; a magnetic storage device; or any suitable combination of the foregoing. In the context of this document, a computer readable storage medium may be any tangible medium that can contain or store a program for use by or in connection with an instruction execution system, apparatus, or device.

It will be appreciated that computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed approximately simultaneously to enhance utilization of the processor and to facilitate substantially simultaneous functions. By way of implementation, any and all methods, program codes, program instructions, and the like described herein may be implemented in one or more threads which may in turn spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States then the method is considered to be performed in the United States by virtue of the causal entity.

While the invention has been disclosed in connection with preferred embodiments shown and described in detail, various modifications and improvements thereon will become apparent to those skilled in the art. Accordingly, the foregoing examples should not limit the spirit and scope of the present invention; rather it should be understood in the broadest sense allowable by law.

What is claimed is:

1. A processor-implemented method for robotic control comprising:

obtaining, using a first computing device, cognitive state data for an individual including facial data for the individual;

collecting voice data from the individual and augmenting the cognitive state data with the voice data, wherein the voice data includes speech rate;

learning, using a second computing device, a cognitive state profile for the individual using the cognitive state data that was obtained;
collecting further cognitive state data for the individual;
comparing the further cognitive state data with the cognitive state profile; and
providing stimuli by a first robot to the individual based on the comparing.

2. The method of claim 1 wherein the facial data is obtained from a camera located outside of the first robot.

3. The method of claim 1 wherein the obtaining the cognitive state data is accomplished from a repository of cognitive state information for the individual.

4. The method of claim 1 wherein the obtaining the cognitive state data is accomplished using a camera which is located in a room occupied by the individual.

5. The method of claim 1 wherein the obtaining the cognitive state data is accomplished by one or more people providing data input about the individual.

6. The method of claim 1 wherein the cognitive state profile is initialized based on demographic data.

7. The method of claim 1 wherein the learning the cognitive state profile includes augmenting an existing cognitive state profile based on the cognitive state data that was obtained.

8. The method of claim 1 wherein the cognitive state profile includes use patterns for the first robot.

9. The method of claim 1 wherein the further cognitive state data includes further facial data for the individual.

10. The method of claim 1 wherein the further cognitive state data includes audio data for the individual.

11. The method of claim 1 wherein the cognitive state profile includes information on usage time for the first robot.

12. The method of claim 1 wherein the augmenting is based on lexical analysis of the voice data that looks at sentiment.

13. The method of claim 1 further comprising performing voice recognition for the individual.

14. The method of claim 1 wherein the facial data is obtained from a camera inside of the first robot.

15. The method of claim 1 further comprising deriving demographic data from the facial data.

16. The method of claim 15 wherein the demographic data that is derived is augmented by setup parameters of the first robot.

17. The method of claim 1 wherein the obtaining cognitive state data for the individual is accomplished using a second robot.

18. The method of claim 1 further comprising transferring the cognitive state profile to the first robot.

19. The method of claim 18 further comprising transferring the cognitive state profile from a second robot to the first robot.

20. The method of claim 1 wherein the cognitive state profile is further learned based on input from the first robot and a second robot.

21. The method of claim 20 wherein the learning is accomplished on the first robot with stimuli being provided by the second robot.

22. The method of claim 21 wherein the stimuli being provided by the second robot are based on the learning on the first robot.

23. The method of claim 1 further comprising performing facial recognition for the individual.

24. A computer program product embodied in a non-transitory computer readable medium for robotic control, the computer program product comprising code which causes one or more processors to perform operations of:
obtaining cognitive state data for an individual including facial data for the individual;
collecting voice data from the individual and augmenting the cognitive state data with the voice data, wherein the voice data includes speech rate;
learning a cognitive state profile for the individual using the cognitive state data that was obtained;
collecting further cognitive state data for the individual;
comparing the further cognitive state data with the cognitive state profile; and
providing stimuli by a first robot to the individual based on the comparing.

25. A computer system for robotic control comprising:
a memory which stores instructions;
one or more processors coupled to the memory wherein the one or more processors, when executing the instructions which are stored, are configured to:
obtain cognitive state data for an individual including facial data for the individual;
collect voice data from the individual and augment the cognitive state data with the voice data, wherein the voice data includes speech rate;
learn a cognitive state profile for the individual using the cognitive state data that was obtained;
collect further cognitive state data for the individual;
compare the further cognitive state data with the cognitive state profile; and
provide stimuli by a first robot to the individual based on the comparing.

* * * * *